United States Patent
Huang et al.

(10) Patent No.: US 12,364,418 B2
(45) Date of Patent: Jul. 22, 2025

(54) METHOD FOR MANUFACTURING IMPLANTABLE MICRO-BIOSENSOR

(71) Applicant: BIONIME CORPORATION, Taichung (TW)

(72) Inventors: Chun-Mu Huang, Taichung (TW); Chieh-Hsing Chen, Taichung (TW); Heng-Chia Chang, Taichung (TW); Chi-Hao Chen, Taichung (TW); Chien-Chung Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 1234 days.

(21) Appl. No.: 16/983,117

(22) Filed: Aug. 3, 2020

(65) Prior Publication Data
US 2021/0030316 A1    Feb. 4, 2021

Related U.S. Application Data

(60) Provisional application No. 62/882,162, filed on Aug. 2, 2019.

(51) Int. Cl.
*A61B 5/1473* (2006.01)
*A61B 5/1486* (2006.01)

(52) U.S. Cl.
CPC ........ *A61B 5/1473* (2013.01); *A61B 5/14865* (2013.01); *A61B 2562/125* (2013.01); *Y10T 29/49002* (2015.01); *Y10T 29/49826* (2015.01)

(58) Field of Classification Search
CPC .............. A61B 5/14503; A61B 5/1473; A61B 5/14865
See application file for complete search history.

(56) References Cited

U.S. PATENT DOCUMENTS

| | | |
|---|---|---|
| 6,616,819 B1 | 9/2003 | Liamos et al. |
| 8,326,393 B2 | 12/2012 | Kotzan et al. |
| 9,351,677 B2 | 5/2016 | Rong et al. |
| 9,743,871 B2 | 8/2017 | Simpson et al. |
| 2002/0179441 A1 | 12/2002 | Yamanishi et al. |

(Continued)

FOREIGN PATENT DOCUMENTS

| | | |
|---|---|---|
| CN | 104825171 A | 8/2015 |
| CN | 105943058 A | 9/2016 |

(Continued)

OTHER PUBLICATIONS

Search Report issued to European counterpart application No. 20189113.2 by the EPO on Nov. 19, 2020.

*Primary Examiner* — Livius R. Cazan
(74) *Attorney, Agent, or Firm* — Perkins Coie LLP; Viola Kung; Gautam Thatte

(57) ABSTRACT

A method for manufacturing an implantable micro-biosensor includes the steps of: a) providing a substrate, b) forming on a first surface of the substrate a first working electrode which at least includes a first sensing section including a first conductive material, c) forming on the first surface of the substrate at least one second working electrode which at least includes a second sensing section disposed proximate to at least one side of the first sensing section, and d) forming a chemical reagent layer which at least covers the first conductive material of the first sensing section and which reacts with the analyte to produce a product.

18 Claims, 35 Drawing Sheets

(56) References Cited

U.S. PATENT DOCUMENTS

| | | | |
|---|---|---|---|
| 2010/0230285 A1* | 9/2010 | Hoss | A61B 5/14532 600/347 |
| 2011/0259741 A1* | 10/2011 | Murase | A61B 5/14865 204/403.01 |
| 2013/0245412 A1 | 9/2013 | Rong et al. | |
| 2015/0241378 A1 | 8/2015 | Liu et al. | |
| 2016/0116429 A1* | 4/2016 | Murase | H05K 1/0313 174/251 |
| 2017/0055892 A1 | 3/2017 | Little et al. | |
| 2018/0199873 A1 | 7/2018 | Wang et al. | |
| 2020/0305740 A1 | 10/2020 | Quan et al. | |

FOREIGN PATENT DOCUMENTS

| | | |
|---|---|---|
| CN | 105411607 B | 3/2017 |
| WO | 2005045413 A1 | 5/2005 |
| WO | 2010099154 A2 | 9/2010 |

* cited by examiner (a)

(b)

METHOD FOR MANUFACTURING IMPLANTABLE MICRO-BIOSENSOR

CROSS-REFERENCE TO RELATED APPLICATION

This application claims priority of U.S. Provisional Application No. 62/882,162, filed on Aug. 2, 2019, which is incorporated by reference herein in its entirety.

FIELD

The disclosure relates to a method for manufacturing an implantable micro-biosensor.

BACKGROUND

The rapid increase in the population of diabetic patients emphasizes the need to monitor and control the variation of glucose concentration in a body of a subject. As a result, many studies are moving towards the development of implantable continuous glucose monitoring systems, so as to address the inconvenience associated with repeated procedures of blood collection and tests. The basic configuration of the continuous glucose monitoring system includes a biosensor and a transmitter. The biosensor measures a physiological signal in response to a glucose concentration in the body, and the measurement thereof is mostly based on an electrochemical process. Specifically, glucose is subjected to a catalysis reaction with glucose oxidase (GOx) to produce gluconolactone and a reduced glucose oxidase, followed by an electron transfer reaction between the reduced glucose oxidase and oxygen in a biological fluid of the body to produce hydrogen peroxide ($H_2O_2$) as a byproduct. The glucose concentration is then derived from an oxidation reaction of the byproduct $H_2O_2$. The reaction mechanism of the electrochemical process is shown below.

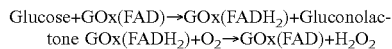

Glucose+GOx(FAD)→GOx(FADH$_2$)+Gluconolactone GOx(FADH$_2$)+O$_2$→GOx(FAD)+H$_2$O$_2$ In the above reaction mechanism, FAD (i.e., flavin adenine dinucleotide) is an active center of GOx.

However, if interfering substances, such as ascorbic acid (a major component of vitamin C), acetaminophen (a common analgesic ingredient), uric acid, protein, glucose analogs, or the like, are present in the blood or the tissue fluid and the oxidation potentials thereof are proximate to the oxidation potential of $H_2O_2$, the measurement of glucose concentration will be adversely affected. Therefore, it is difficult to ensure that the physiological parameters of a subject are truly reflected by the measurement values and to maintain a long-term stability of the measured signal when the continuous glucose monitoring system is in operation.

At present, the aforesaid shortcomings are solved, for example, by providing a polymer membrane to filter out the interfering substances. However, it remains difficult to filter out the interfering substances completely. Alternatively, a plurality of working electrodes optionally coated with an enzyme or different types of enzymes are respectively applied with potentials to read a plurality of signals from the working electrodes. The signals are then processed to accurately obtain the physiological parameter of the analyte. However, such conventional processes, which involves the use of the working electrodes, are very complicated.

In addition, stable sensing potentials can be obtained by using a silver/silver chloride as a material of the reference electrode or the counter/reference electrode. Silver chloride of the reference electrode or the counter electrode should be maintained at a minimal amount without being completely consumed, so as to permit the biosensor to be stably maintained in a test environment for measuring the physiological signal and for achieving a stable ratio relationship between the physiological signal and the physiological parameter of the analyte to be detected.

However, silver chloride would be dissolved, resulting in the loss of chloride ions, which will cause a shift of the reference potential. When the silver/silver chloride is used for the counter electrode so as to be actually involved in a redox reaction, silver chloride would be even more consumed by reduction of silver chloride to silver. Accordingly, the service life of the biosensor is often limited by the amount of silver chloride on the reference electrode or the counter electrode. The problem is addressed by many prior arts. For example, in the two-electrode system, the counter electrode has a consumption amount of about 1.73 mC/day (microcoulomb/day) under an average sensing current of 20 nA (nanoampere). That is, if the biosensor is intended to be buried under the skin of the body for continuously monitoring glucose for 16 days, a minimum consumption capacity of 27.68 mC is required. Therefore, existing technology attempts to increase the length of the counter electrode to be greater than 10 mm. However, in order to avoid being implanted deeply into subcutaneous tissue, the biosensor needs to be implanted at an oblique angle, which results in problems such as a larger wound, a higher infection risk, and the like. In addition, the pain caused by the implantation is more pronounced.

Along with the development of a miniaturized version of the continuous glucose monitoring system, development of a biosensor that can improve the measurement accuracy, extend the service life, simplify the manufacturing process, and reduce the manufacturing cost, is an urgent goal to be achieved.

SUMMARY

Therefore, an object of the disclosure is to provide a method for manufacturing an implantable micro-biosensor which has an accurate measurement and an extended service life and which can monitor a physiological parameter of an analyte continuously.

According to the disclosure, there is provided a method for manufacturing an implantable micro-biosensor, which includes the steps of:

a) providing a substrate having a first surface, wherein the first surface has a first sensing region to be implanted subcutaneously for measuring a physiological parameter of an analyte in a biological fluid;

b) forming on the first surface of the substrate a first working electrode which at least includes a first sensing section, a surface material of the first sensing section including a first conductive material;

c) forming on the first surface of the substrate at least one second working electrode which at least includes a second sensing section disposed proximate to at least one side of the first sensing section, a surface material of the second sensing section including a second conductive material different from the first conductive material, wherein both the second sensing section and the first sensing section are located at the first sensing region; and d) forming a chemical reagent layer which at least covers the first conductive material of the first sensing section and which reacts with the analyte to produce a product.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
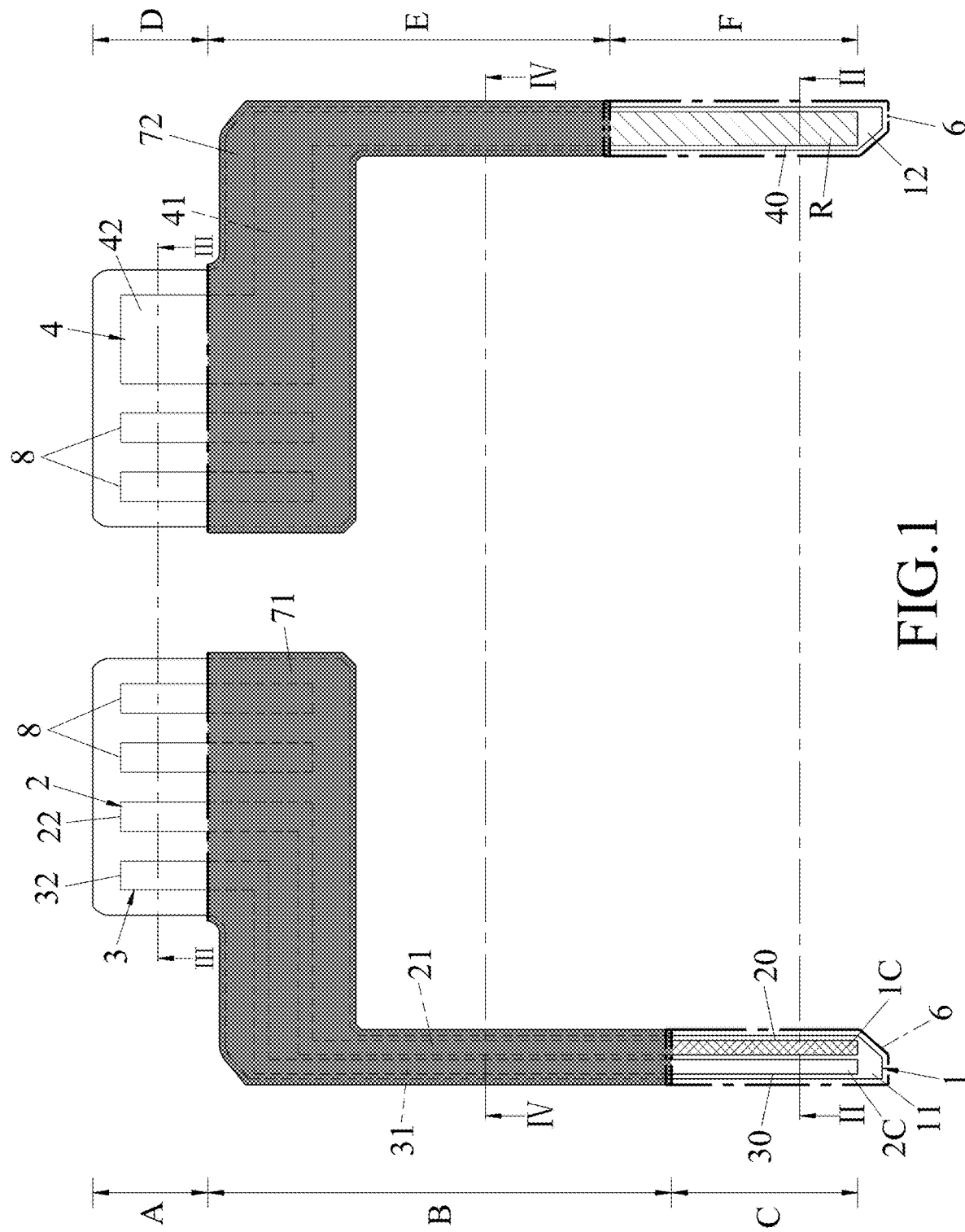
FIG. 1 is a schematic view illustrating Embodiment 1 of an implantable micro-biosensor according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

The term "analyte" as used herein refers to any substance to be detected that exists in an organism, for example, glucose, lactose, and uric acid, but are not limited thereto. In the embodiments illustrated below, the analyte is glucose. In certain embodiments, the implantable micro-biosensor is an implantable glucose micro-biosensor, which is used for detecting a concentration of glucose in an interstitial fluid of a body. The term "a biological fluid" as used herein may be, for example, the interstitial fluid, but is not limited thereto. The term "a physiological parameter" as used herein may be, for example, a concentration, but is not limited thereto.

The term "at least one" as used herein will be understood to include one as well as any quantity more than one.

A method for manufacturing an implantable micro-biosensor according to the disclosure includes the steps of:

a) providing a substrate having a first surface, wherein the first surface has a first sensing region to be implanted subcutaneously for measuring a physiological parameter of an analyte in a biological fluid;

b) forming on the first surface of the substrate a first working electrode which at least includes a first sensing section, a surface material of the first sensing section including a first conductive material;

c) forming on the first surface of the substrate at least one second working electrode which at least includes a second sensing section disposed proximate to at least one side of the first sensing section, a surface material of the second sensing section including a second conductive material different from the first conductive material, wherein both the second sensing section and the first sensing section are located at the first sensing region; and d) forming a chemical reagent layer which at least covers the first conductive material of the first sensing section and which reacts with the analyte to produce a product.

In certain embodiments, steps b) and c) are implemented simultaneously by the sub-steps of:

b1) applying the second conductive material on the first surface of the substrate;

b2) subjecting the second conductive material to patterning so as to divide the second conductive material into a first area and at least one second area separated from each other; and b3) applying the first conductive material at the first sensing region to cover at least a portion of the second conductive material of the first area to form the first sensing section of the first working electrode and to configure the second conductive material at the second area as the at least one second working electrode.

In certain embodiments, the step b) further includes after the sub-step of b2), a sub-step of forming a first insulation layer on the first surface of the substrate so as to define the first sensing region on the first surface of the substrate.

In certain embodiments, the sub-step of b2) permits the second sensing section to be spaced apart from the at least one side of the first sensing section by a distance of up to 0.2 mm.

In certain embodiments, the sub-step of b2) permits the second sensing section to extend along and be spaced apart from at least a portion of a periphery of the first sensing section, such that a ratio of the portion of the periphery of the first sensing section to a total of the periphery of the first sensing section ranges from 30% to 100%.

In certain embodiments, the sub-step of b2) forms two of the second areas so as to permit two of the second sensing sections of two of the second working electrodes to be formed in the sub-step b3). The second sensing sections of the second working electrodes are disposed, respectively, along two opposite sides of the first sensing section of the first working electrode.

In certain embodiments, the sub-step b1) is implemented by a screen printing process.

In certain embodiments, the sub-step b3) is implemented by a plating process.

In certain embodiments, the sub-step b2) is implemented by a laser engraving process.

In certain embodiments, step d) is implemented by immersing the substrate formed with the first and second work electrodes into a solution containing a chemical reagent.

In certain embodiments, the chemical reagent simultaneously covers the first conductive material of the first sensing section and the second conductive material of the second sensing section.

In certain embodiments, the first working electrode is driven so as to permit the first conductive material to have a first sensitivity responsive to the product. The second working electrode is driven so as to permit the second conductive material to have a second sensitivity that is responsive to the product and that is smaller than the first sensitivity.

In certain embodiments, the first conductive material is selected from the group consisting of a noble metal, a noble metal derivative, and a combination thereof, and the noble metal is selected from the group consisting of gold, platinum, palladium, iridium, and combinations thereof.

In certain embodiments, the method according to the disclosure further includes a step of e) forming on the substrate a counter electrode which cooperates with the first work electrode to measure the physiological parameter of the analyte.

In certain embodiments, the method according to the disclosure further includes a step of f) forming on the substrate a reference electrode which is spaced apart from the counter electrode and which is free of electrical connection with the counter electrode.

In certain embodiments, the steps of e) and f) are implemented simultaneously by the sub-steps of:

i) forming a backing material layer on a second surface of the substrate which is opposite to the first surface of the first surface;

ii) subjecting the backing material layer to patterning so as to divide the backing material layer into a third area and a fourth area which are separated from each other and which are free of electrical connection with each other, such that the backing material layer at the third area is configured as the counter electrode; and iii) forming a reference electrode material on at least a portion of the backing material layer at the fourth area to obtain the reference electrode.

In certain embodiments, the method according to the disclosure further includes a sub-step after the sub-step ii), of forming a second insulation layer on the second surface of the substrate so as to define a second sensing region.

In certain embodiments, the steps of e) and f) are implemented simultaneously by the sub-steps of:

i') forming a backing material layer on a second surface of the substrate which is opposite to the first surface of the substrate;

ii') applying a precursor material on at least a portion of the backing material layer;

iii') subjecting the backing material layer and the precursor material to patterning so as to divide the second surface into a third area and a fourth area which are separated from each other and which are free of electrical connection with each other, such that the backing material layer at the third area is configured as the counter electrode and at least a portion of the backing material layer at the fourth area is covered with the precursor material; and iv') converting the precursor material on the backing material layer at the fourth area to a reference electrode material to obtain the reference electrode.

In certain embodiments, the backing material layer is formed as a layered-configuration selected from the group consisting of a single-layered configuration and a multi-layered configuration, each of which is made from a material selected from the group consisting of carbon, silver, a combination thereof.

In certain embodiments, the method according to the disclosure further includes a sub-step after the sub-step iii'), of forming a second insulation layer on the second surface of the substrate so as to define a second sensing region.

Electrode Configuration and Manufacturing Process of Implantable Micro-Biosensor:

Embodiment 1

Referring to FIG. 1, a first surface of Embodiment 1 of an implantable micro-biosensor according to the disclosure includes o a first signal output region (A) to be connected to a transmitter (not shown), a first sensing region (C) for measuring a physiological parameter (for example, a concentration) of an analyte (for example, glucose) in a body, and a first signal connecting region (B) for interconnecting the first signal output region (A) and the first sensing region (C). The implantable micro-biosensor is operated perpendicularly to the skin of the body and is partially implanted into the body, and has an implanting end portion, which at least includes the first sensing region (C). Specifically, the implanting end portion has a length which is sufficient to at least reach dermis of the skin to measure a glucose concentration in the interstitial fluid. In certain embodiments, the length of the implanting end portion is up to 6 mm. In certain embodiments, in order to have advantages of avoiding foreign body sensation, forming a smaller implantation wound, reducing pain sensation, and the like, the length of the implanting end portion is up to 5 mm. In certain embodiments, the length of the implanting end portion is up to 4.5 mm. In certain embodiments, the length of the implanting end portion is up to 3.5 mm. More specifically, in certain embodiments, the first sensing region (C) has a length ranging from 2 mm to 6 mm. In certain embodiments, the length of the first sensing region (C) ranges from 2 mm to 5 mm. In certain embodiments, the length of the first sensing region (C) ranges from 2 mm to 4.5 mm. In certain embodiments, the length of the first sensing region (C) ranges from 2 mm to 3.5 mm. In certain embodiments, the first sensing region (C) has a width ranging from 0.01 mm to 0.5 mm. In certain embodiments, the width of the first sensing region (C) is less than 0.3 mm.

Referring to FIGS. 1 to 4, Embodiment 1 of the implantable micro-biosensor according to the disclosure includes a substrate 1, a first working electrode 2, a second working electrode 3, a counter electrode 4, a chemical reagent layer 6 for reacting with glucose in a body to produce hydrogen peroxide, and an insulation unit 7, which includes a first insulation layer 71 and a second insulation layer 72.

The substrate 1 has a first surface 11 and a second surface 12 opposite to the first surface 11. The substrate 1 may be made of any material which is useful for making an electrode substrate and which has flexibility and insulation properties. Example of the material for making the substrate 1 may be polyester, polyimide, and the like, and combinations thereof, but are not limited thereto.

The first working electrode 2 is disposed on the first surface 11 of the substrate 1, and includes a first sensing section 20 located at the first sensing region (C) and covered by the chemical reagent layer 6, a first connecting section 21 located at the first signal connecting region (B), and a first output section 22 located at the first signal output region (A). A surface material of the first sensing section 20 at least includes a first conductive material 1C. The first sensing section 20 is driven by a first potential difference to permit the first conductive material 1C to react with hydrogen peroxide, which is a product of a reaction of the chemical reagent layer 6 with glucose, to produce a current signal. A physiological signal in response to a glucose concentration is obtained when a ratio relationship between the value of the current signal and the concentration of hydrogen peroxide is achieved.

Examples of the first conductive material 1C include carbon, platinum, aluminum, gallium, gold, indium, iridium, iron, lead, magnesium, nickel, molybdenum, osmium, palladium, rhodium, silver, tin, titanium, zinc, silicon, zirconium, combinations thereof, and derivatives thereof (for example, alloys, oxides, metal compounds, or the like). In certain embodiments, the first conductive material 1C is a noble metal, a derivative thereof, or a combination thereof.

The second working electrode 3 is disposed on the first surface 11 of the substrate 1, and includes a second sensing section 30, a second connecting section 31, and a second output section 32. The second sensing section 30 is disposed proximate to the first sensing section 20 and is located at the first sensing region (C). The second connecting section 31 is located at the first signal connecting region (B). The second output section 32 is located at the first signal output region (A). A surface material of the second sensing section 30 at least includes a second conductive material 2C. The second sensing section 30 is driven by a second potential difference to permit the second conductive material 2C to consume at least a portion of an interfering substance in the body which approaches the second sensing section 30. Examples of the second conductive material 2C may be the same as those described above for the first conductive material 1C.

Figure 5:
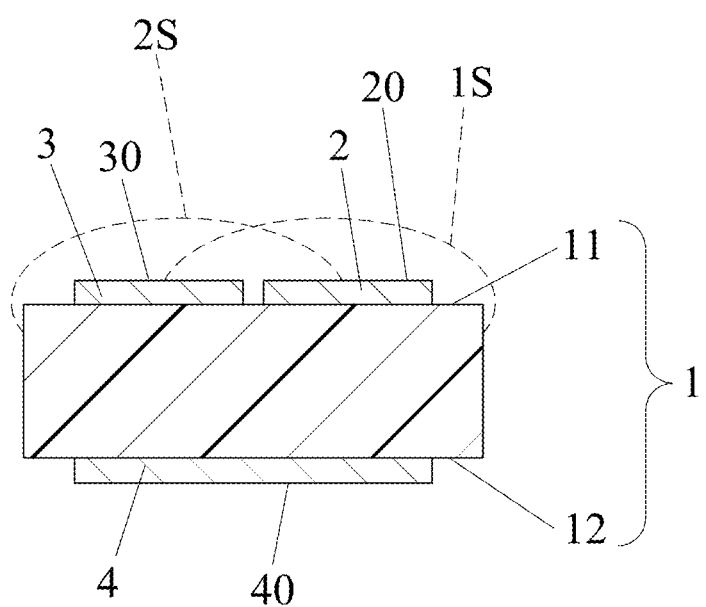
FIG. 5 is a schematic section view illustrating an interaction between a first sensing section and a second sensing section of Embodiment 1.

Referring to FIG. 5, it should be understood that when the first working electrode 2 is driven by the first potential difference to perform an electrochemical reaction, the first sensing section 20 cannot only form a measuring region 1 around its surface for measuring the hydrogen peroxide within the measuring region 1S, but also react with the interfering substance in a biological fluid of the body to produce an interfering circuit signal, which will be outputted together with the circuit signal to cause an interference to the physiological signal. When the second working electrode 3 is driven by the second potential difference, an interfering substance approaching a surface of the second sensing section 30 is consumed via an electrochemical reaction to permit the concentration of the interfering substance to have a concentration gradient which decreases gradually along a direction toward the surface of the second sensing section 30, thereby forming at least one interference-eliminating region 2S. Since the second sensing section 30 is proximate to the first sensing section 20, the interference-eliminating region 2S is in touch with a surrounding of the first sensing section 20 and can at least partially overlap with the measuring region 1S, such that the interfering substance approaching the first and second sensing sections 20, 30 can be consumed simultaneously. In order to permit the interference-eliminating region 2S to sufficiently overlap with the measuring region 1S, in the first sensing region (C), the second sensing section 30 of the second working electrode 3 is disposed along and spaced apart from at least one side of the first sensing section 20 of the first working electrode 2 by a distance of up to 0.2 mm, so as to reduce the interference caused by the interfering substance to the measurement of the glucose concentration. In certain embodiments, the distance ranges from 0.01 mm to 0.2 mm. In certain embodiments, the distance ranges from 0.01 mm to 0.1 mm. In certain embodiments, the distance ranges from 0.02 mm to 0.05 mm.

Furthermore, when the second working electrode 3 is driven by the second potential difference, the second conductive material 2C may react with hydrogen peroxide to produce another current signal, such that some of the hydrogen peroxide which should be sensed by the first working electrode 2 so as to accurately measure the concentration of the analyte is consumed by the second working electrode 3, causing a negative affect on the accurate measurement of the concentration of the analyte. Therefore, when the first conductive material 1C of the first working electrode 2 is driven by the first potential difference to have a first sensitivity in response to hydrogen peroxide and the second conductive material 2C of the second working electrode 3 is driven by the second potential difference to have a second sensitivity, the first sensitivity of the first conductive material 1C should be greater than the second sensitivity of the second conductive material 2C. Therefore, the first conductive material 1C is different from the second conductive material 2C. In certain embodiments, the first conductive material 1C may be a noble metal, such as gold, platinum, palladium, iridium, or combinations thereof. Desirably, the second conductive material 2C does not has any sensitivity to hydrogen peroxide and may be, but not limited to, carbon, nickel, copper and so on.

In Embodiment 1, the first conductive material 1C is platinum, the first potential difference ranges from 0.2 V (volt) to 0.8 V, for example, 0.4 V to 0.7 V. The second conductive material 2C is carbon. The second potential difference ranges from 0.2 V to 0.8 V, for example, 0.4 V to 0.7 V. The first potential difference may be the same as the second potential difference.

Figure 6:
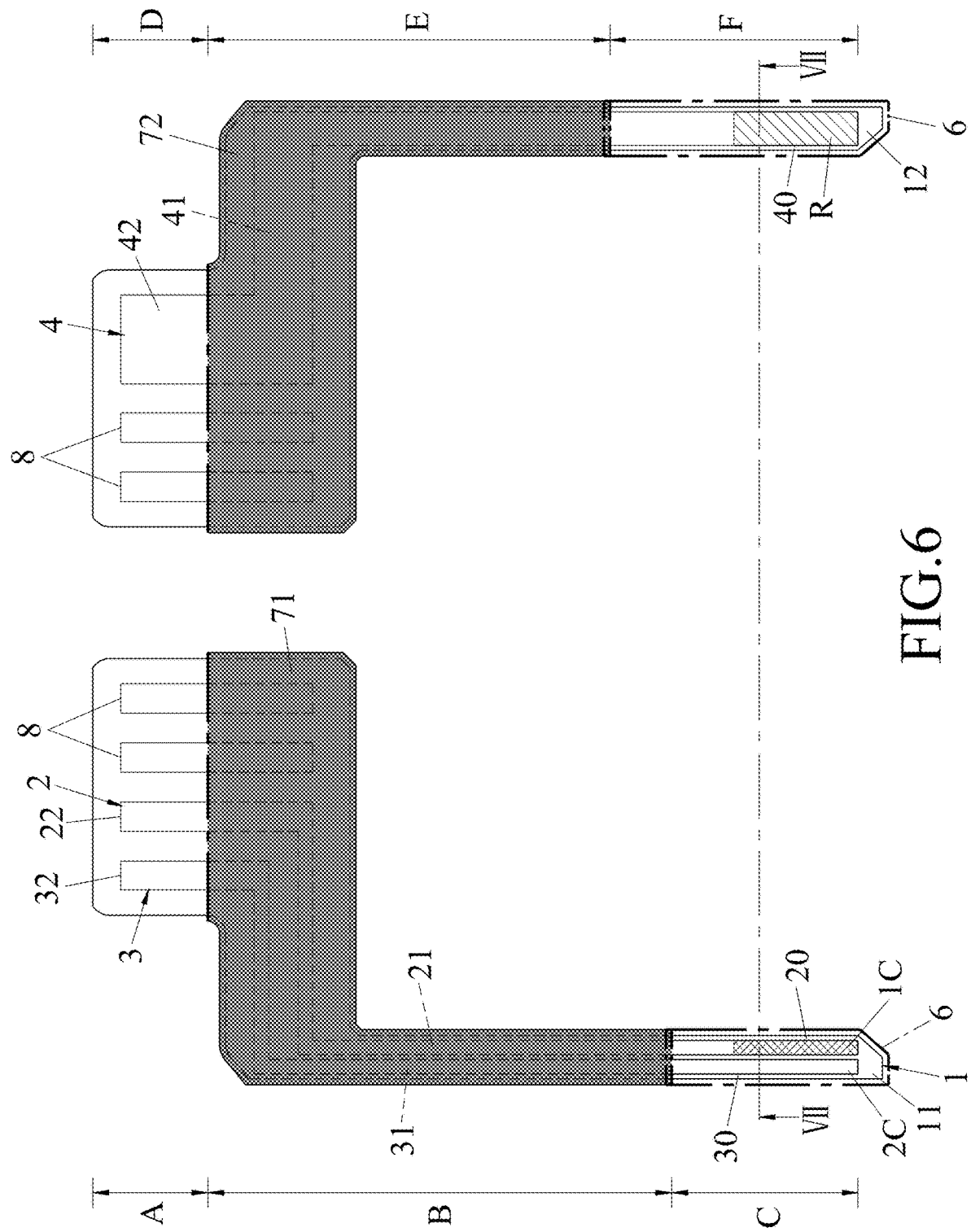
FIG. 6 is a schematic view illustrating a configuration of a variation of Embodiment 1.

Referring to FIG. 6, although the first conductive material 1C is formed at all the first sensing region (C), it is available to have only a portion of the first working electrode 2 formed with the first conductive material 1C in the first sensing region (C).

Return to FIG. 1, a second surface of Embodiment 1 of the implantable micro-biosensor according the disclosure includes a second signal output region (D), a second signal connecting region (E), and a second sensing region (F). The counter electrode 4 is disposed on the second surface 12 (that is, the second surface of the implantable micro-biosensor) of the substrate 1, and includes a third sensing section 40 located at the second sensing region (F), a third connecting section 41 located at the second signal connecting region (E), and a third output section 42 located at the second signal output region (D), so as to cooperate with the first working electrode 2 to measure the physiological signal, and to cooperate with the second working electrode 3 to consume the interfering substance. It should be understood that the counter electrode 4 is not limited to be disposed on the second surface 12, and may be disposed on the first surface 11 as long as the aforesaid cooperation thereof with each of the first and second working electrodes 2, 3 can be satisfied. When the counter electrode 4 is disposed on the second surface 12, the width of the implantable micro-biosensor can be decreased. In addition, the counter electrode 4 may cooperate selectively with the first working electrode 2 or the second working electrode 3 to regenerate silver halide.

In Embodiment 1, the material for the counter electrode 4 includes a silver/silver halide (R) so as to permit the counter electrode 4 to function as a reference electrode as well. That is, the counter electrode 4 can be cooperated with the first working electrode 2 to from a loop so as to allow the electrochemical reaction occurring at the first working electrode 2 and to provide a stable relative potential as a reference potential. A non-limiting example of the silver halide is silver chloride, and silver iodide is also available. In view to reduce the production cost and enhance the biological compatibility of the implantable micro-biosensor of the disclosure, the silver/silver halide (R) may be included only on the surface of the counter electrode 4. The silver/silver halide (R) may be blended with a carbon material (for example, a carbon paste) in a suitable ratio as long as the counter electrode 4 can execute the intended function.

Figure 7:
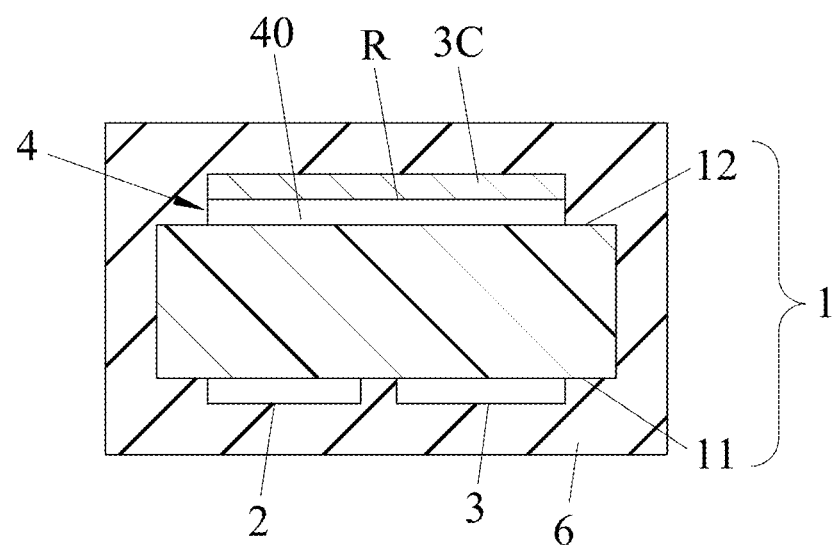
FIG. 7 is a schematic sectional view taken along line VII-VII of FIG. 6.

The amount of the silver halide in the third sensing section 40 of the counter electrode 4 should be in a safe range, so as to avoid complete consumption of the silver halide and to permit the implantable micro-biosensor of the disclosure to be stably maintained in a test environment for measuring the physiological signal. Therefore, referring to FIG. 7, in order to avoid stripping of the silver halide in the environment of the body, the third sensing section 40 may further include a third conductive material 3C that covers at least a portion of the silver/silver halide (R). The silver/silver halide (R) on the third sensing section 40 that is not covered by the third conductive material 3C can be used for measuring the physiological signal. The term "cover at least a portion" described above refers to partially cover or fully cover. Examples of the third conductive material 3C include carbon, silver, and any other conductive materials that will not affect the intended function of the counter electrode 4.

In addition, in order to miniaturize the implantable micro-biosensor of the disclosure and to maintain the amount of the silver halide in a safe range, a third potential difference may be applied between the counter electrode 4 and the first working electrode 2 or between the the counter electrode 4 and the second working electrode 3 to permit the counter electrode 4 to have a potential higher than that of the first or second working electrode 2, 3, so as to regenerate the silver halide and to maintain the silver halide at the third sensing section 40 of the counter electrode 4 to be in a safe range. Specifically, a weight ratio of silver to silver halide may be, but is not limited to, 95 wt %:5 wt %, 70 wt %:30 wt %, 60 wt %:40 wt %, 50 wt %:50 wt %, 40 wt %:60 wt %, 30 wt %:70 wt %, or 5 wt %:95 wt % based on 100 wt % of a total weight of silver and silver halide. In other words, a weight ratio of the silver halide to the silver/silver halide (R) is greater than 0 and less than 1. In particular, the abovementioned weight ratio ranges between 0.01 and 0.99, more particularly, between 0.1 and 0.9, between 0.2 and 0.8, between 0.3 and 0.7, or between 0.4 and 0.6.

Figure 2:
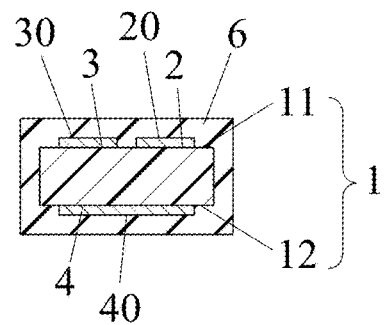
FIG. 2 is a schematic sectional view taken along line II-II of FIG. 1.
Figure 3:
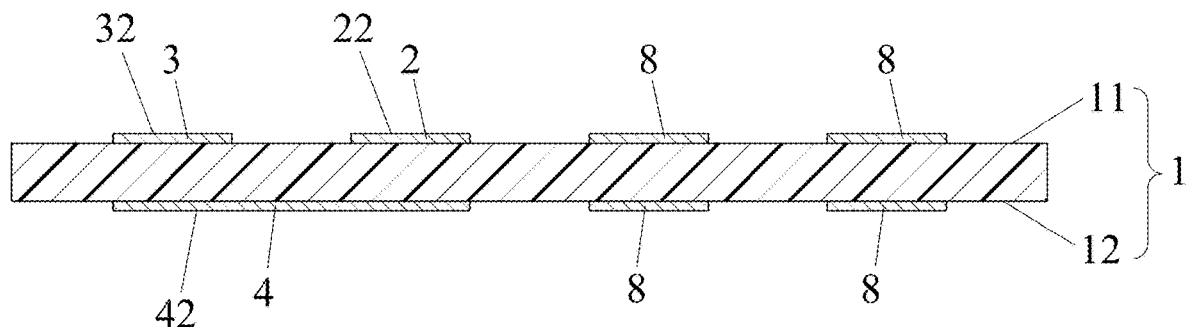
FIG. 3 is a schematic sectional view taken along line III-III of FIG. 1.
Figure 4:
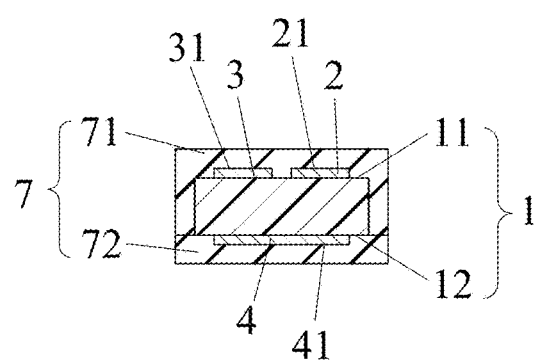
FIG. 4 is a schematic sectional view taken along line IV-IV of FIG. 1.

As described above, the chemical reagent layer 6 covers at least a portion of the first conductive material 1C of the first sensing section 20. Referring specifically to FIG. 2, in Embodiment 1, the chemical reagent layer 6 covers not only the first sensing section 20, but also the second sensing section 30, a portion or whole of the clearance between the first and second sensing sections 20, 30, and the third sensing section 40. In other words, the chemical reagent layer 6 covers at least portions of the first sensing region (C) and the second sensing region (F). The chemical reagent layer 6 includes at least one type of enzyme which is reactive with the analyte or which can enhance a reaction of the analyte with other material. Examples of the enzyme may include glucose oxidase and glucose dehydrogenase, but are not limited thereto. In the disclosure, the first and second working electrodes 2 and 3 are designed such that the chemical reagent layer 6 may not include the mediator.

Except for exposure of the sensing regions (including the first and second sensing regions (C, F)) for signal-sensing and the signal output regions (including the first and second signal output regions (A, D)) for signal-outputting, it is necessary to insulate the first, second, and third signal connecting sections 21, 31, 41 in the signal connecting regions (including the first and second signal connecting regions (B, E)). Therefore, the first insulation layer 71 is located at the first signal connecting region (B), and covers the first connecting section 21 of the first working electrode 2 and the second connecting section 31 of the second working electrode 3. The second insulation layer 72 is located at the second signal connecting region (E), and covers the third connecting section 41 of the counter electrode 4 on the second surface 12 of the substrate 1. The second insulation layer 72 has a length which may be the same as or different from that of the first insulation layer 71. The insulation layer unit 7 may be made of any insulation material, for example, parylene, polyimide, PDMS, LCP or SU-8 of MicroChem, and so on, but is not limited thereto. Each of the first and second insulation layers 71, 72 may have a single-layered or multi-layered configuration. The chemical reagent layer 6 may also cover a portion of the first insulation layer 71 and/or the second insulation layer 72 in addition to the first, second, and third sensing sections 20, 30, 40.

The chemical reagent layer 6, the first insulation layer 71, and the second insulation layer 72 may be covered with a polymer confinement layer (not shown), so as to confine undesirable substances from entering into the implantable micro-biosensor which may affect the measurement of the analyte.

Referring specifically to FIG. 1, each of the first and second signal output regions (A, D) further includes a plurality of electric contact portions 8. Specifically, each of the first and second signal output regions (A, D) includes two of the electric contact portions 8. Two of the electric contact portions 8 are used as a switch set for actuating a power source of the transmitter when the transmitter is electrically connected to the implantable micro-biosensor. The other two of the electric contact portions 8 are used as a mediator for data transmission. It should be understood that the number and the function of the electric contact portions 8 are not limited to the aforesaid.

Figure 8:
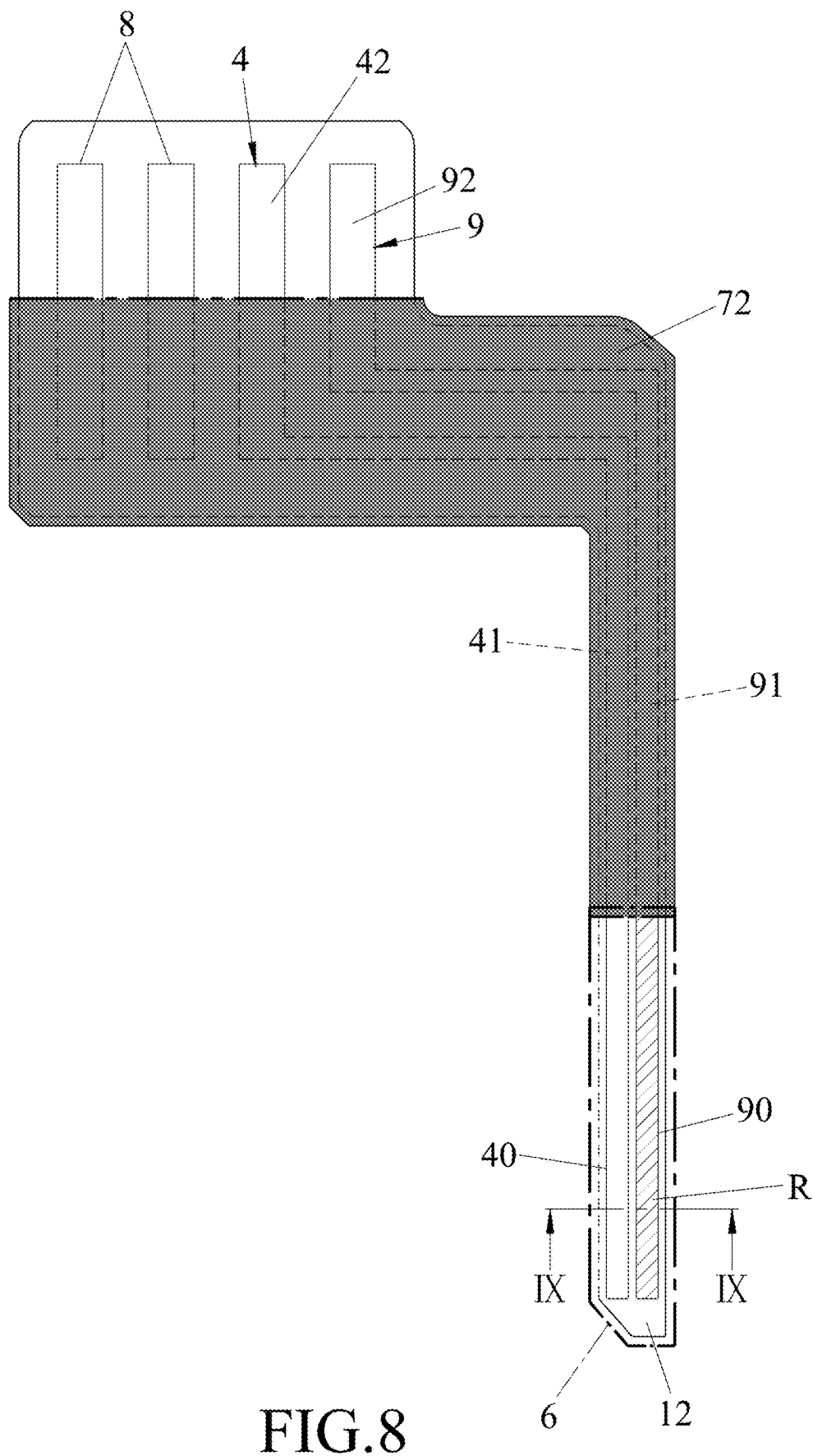
FIG. 8 is a schematic view illustrating a variation of the configuration of the second surface of Embodiment 1.
Figure 9:
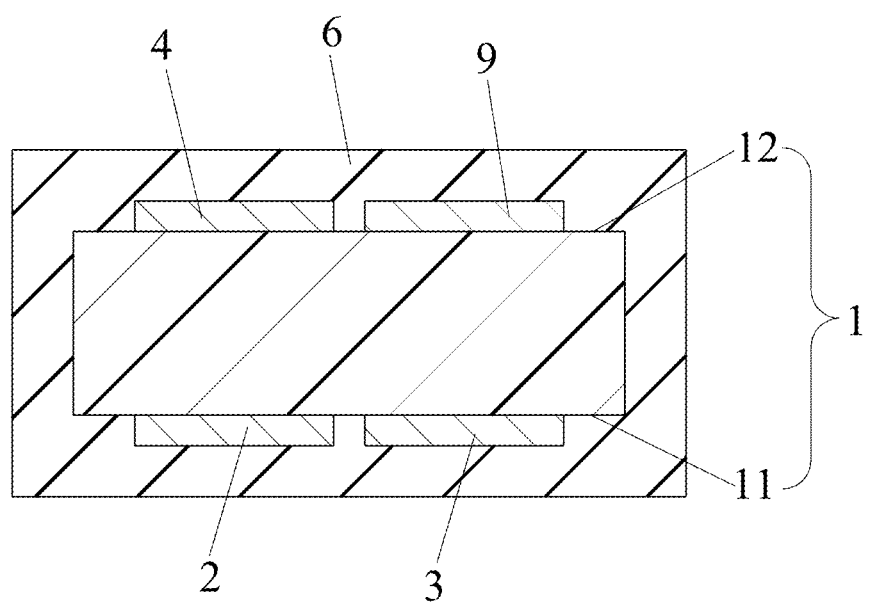
FIG. 9 is a schematic sectional view taken along line IX-IX of FIG. 8.

Referring to FIGS. 8 and 9, Embodiment 1 of the implantable micro-biosensor also can be configured with a reference electrode 9 disposed on the second surface 12 of the substrate 1. The reference electrode 9 includes a fourth sensing section 90 located at the second sensing region (F), a fourth connecting section 91 located at the second signal connecting region (E), and a fourth output section 92 located at the second signal output region (D). Thus, the silver/silver halide (R) of the counter electrode 4 can be omitted and may be at least provided on a surface of the fourth sensing section 90.

Referring specifically to FIGS. 1 to 4, a process for manufacturing Embodiment 1 of the implantable micro-biosensor according to the disclosure includes the steps of:

(A) providing the substrate 1 having the first surface 11;

(B) forming the first work electrode 2 on the first surface 11 of the substrate 1, the first work electrode 2 at least including the first sensing section 20 which includes the first conductive material 1C;

(C) forming the at least one second work electrode 3 on the first surface 11 of the substrate 1, the second work electrode 3 at least including the second sensing section 30, which is disposed proximate to at least one side of the first sensing section 20 and which includes the second conductive material 2C different from the first conductive material 1C;

(D) forming the counter electrode 4 on the substrate 1 so as to cooperate with the first work electrode 2 to measure the physiological parameter of the analyte; and (E) forming the chemical reagent layer 6 which at least covers the first conductive material 1C of the first sensing section 20 so as to react with the analyte to generate a product.

Specifically, the first surface 11 of the substrate 1 includes the first signal output region (A), the first signal connecting region (B), and the first sensing region (C). Steps B) and C) are implemented by the sub-steps of:

(a) applying the second conductive material 2C on the first surface 11 of the substrate 1;

(b) subjecting the second conductive material 2C to patterning according to predetermined sizes, positions, lengths, areas, and the like of the first and second working electrodes 2, 3, to divide the second conductive material 2C into a first area and at least one second area that are separated from each other; and (c) applying the first conductive material 1C at the first sensing region (C) to cover at least a portion of the second conductive material 2C at the first area to form the first sensing section 20 of the first working electrode 2 and to permit the second conductive material 2C at the at least one second area to be configured as the second working electrode 3, which includes the second signal output section 32 located at the first signal output region (A), the second signal connecting section 31 located at the first signal connecting region (B), and the second sensing section 30 located at the first sensing region (C). Therefore, both of the first and second sensing sections 20, 30 in Embodiment 1 manufactured by the abovementioned process are located at the first sensing region (C).

Figure 10:
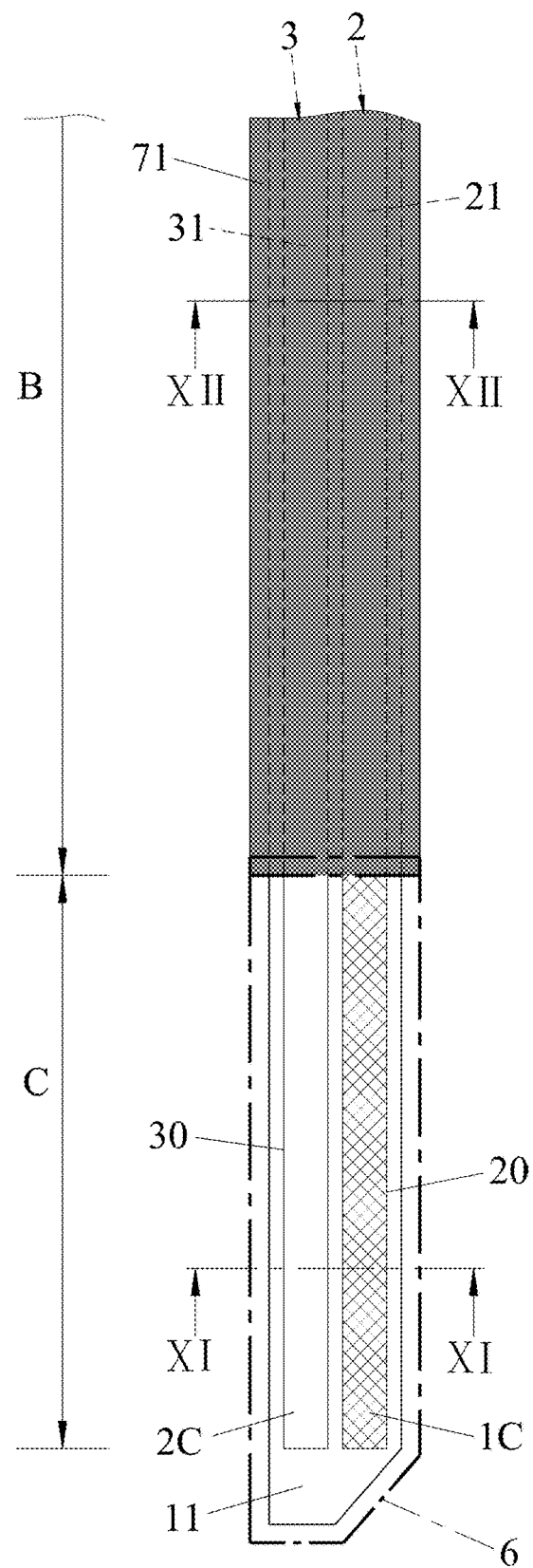
FIG. 10 is a fragmentary schematic view illustrating a variation of the configuration of the first surface of Embodiment 1.
Figure 11:
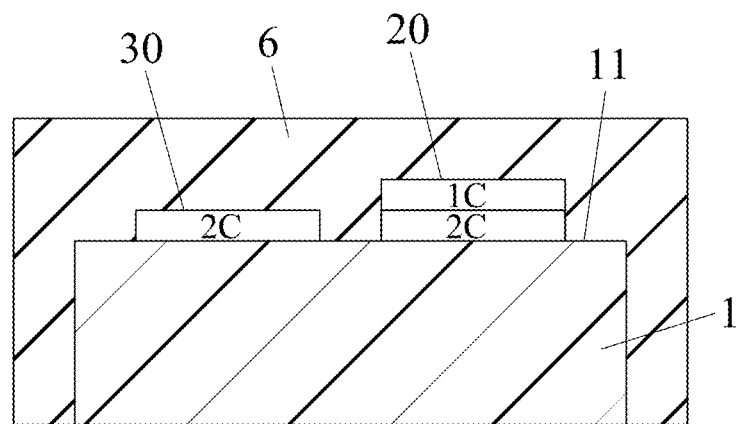
FIG. 11 is a schematic sectional view taken along line XI-XI of FIG. 10.
Figure 12:
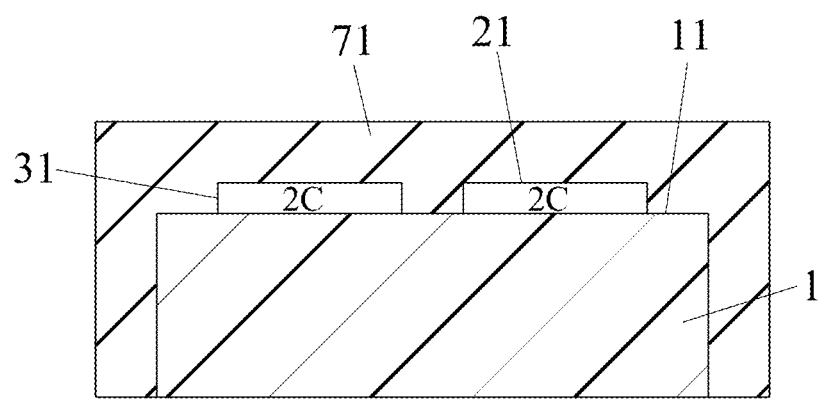
FIG. 12 is a schematic sectional view taken along along line XII-XII of FIG. 10.

Specifically, referring to FIGS. 10 to 12, after sub-step (b), the second conductive material 2C is divided into the first area and the second area which have stripe geometries and which are separated from each other. The second conductive material 2C at the second area extends from the first sensing region (C) through the first signal connecting region (B) to the first signal output region (A), as shown in FIG. 1. After sub-step (c), the first conductive material only covers the second conductive material 2C at the first sensing region (C). Therefore, referring specifically to FIG. 11, the first sensing section 20 of the first working electrode 2 includes a layer of the second conductive material 2C disposed on the first surface 11 of the substrate 1, and a layer of the first conductive material 1C covering the layer of the second conducive material 2C. The first connecting section 21 of the first working electrode 2 only includes the layer of the second conducive material 2C, as shown in FIG. 12. The second working electrode 3 only includes the layer of the second conductive material 2C.

In a variation of Embodiment 1, the first conductive material 1C can only cover a portion of the second conductive material 2C of the first sensing region (C) as shown in FIG. 6 by modification of sub-step (c).

In another variation of Embodiment 1, the first conductive material 1C may not only cover the second conductive material 2C at the first sensing region (C), but also extend to cover a portion of the second conductive material 2C at the first signal connecting region (B) by modification of sub-steps (b) and (c).

In further another variation of Embodiment 1, the second conductive material 2C at the first area may have a length less than that of the second conductive material 2C at the second area by modification of sub-step (b). For example, the second conductive material 2C at the first area may be located only at the first signal output region (A) and the first signal connecting region (B). Thereafter, the first conductive material 1C not only is formed at the first sensing region (C), but also cover the second conductive material 2C at the first signal connecting region (B) by sub-step (c), so as to permit the first sensing section 20 to be connected to the first signal output section 22.

Figure 13:
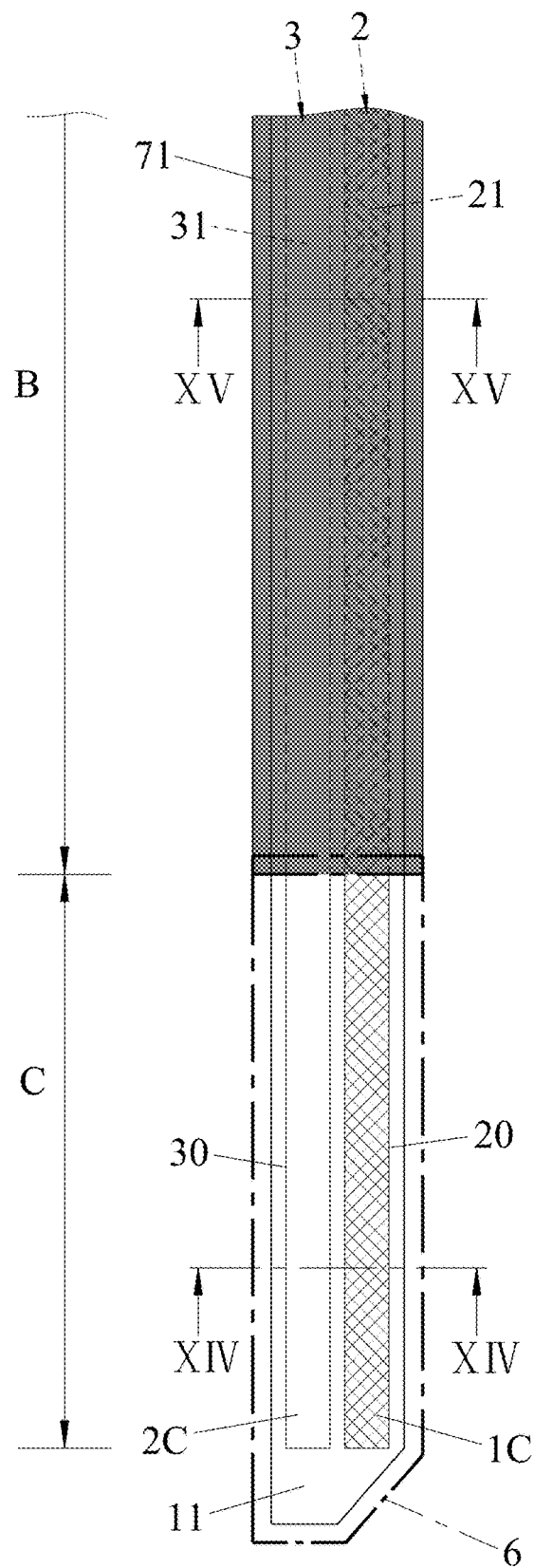
FIG. 13 is a fragmentary schematic view illustrating another variation of the configuration of the first surface of Embodiment 1.
Figure 14:
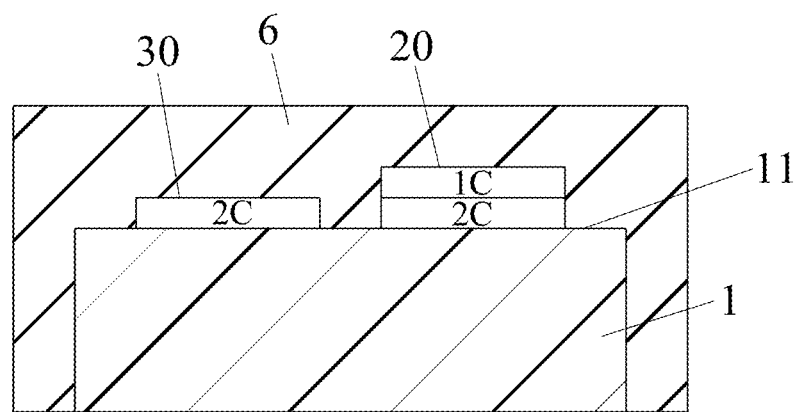
FIG. 14 is a schematic sectional view taken along along line XIV-XIV of FIG. 13.
Figure 15:
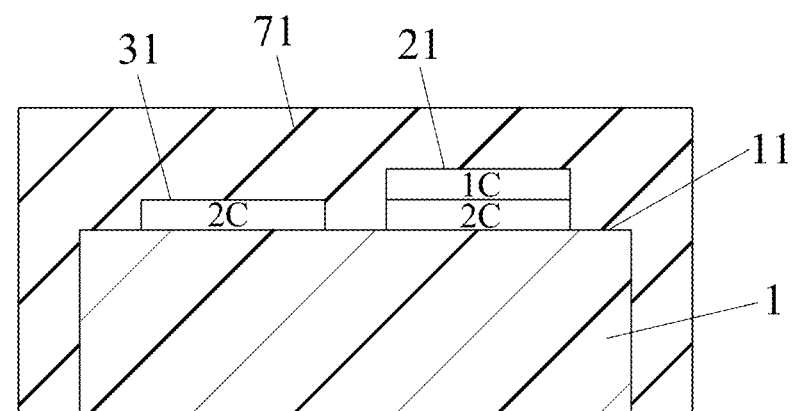
FIG. 15 is a schematic sectional view taken along along line XV-XV of FIG. 13.
Figure 16:
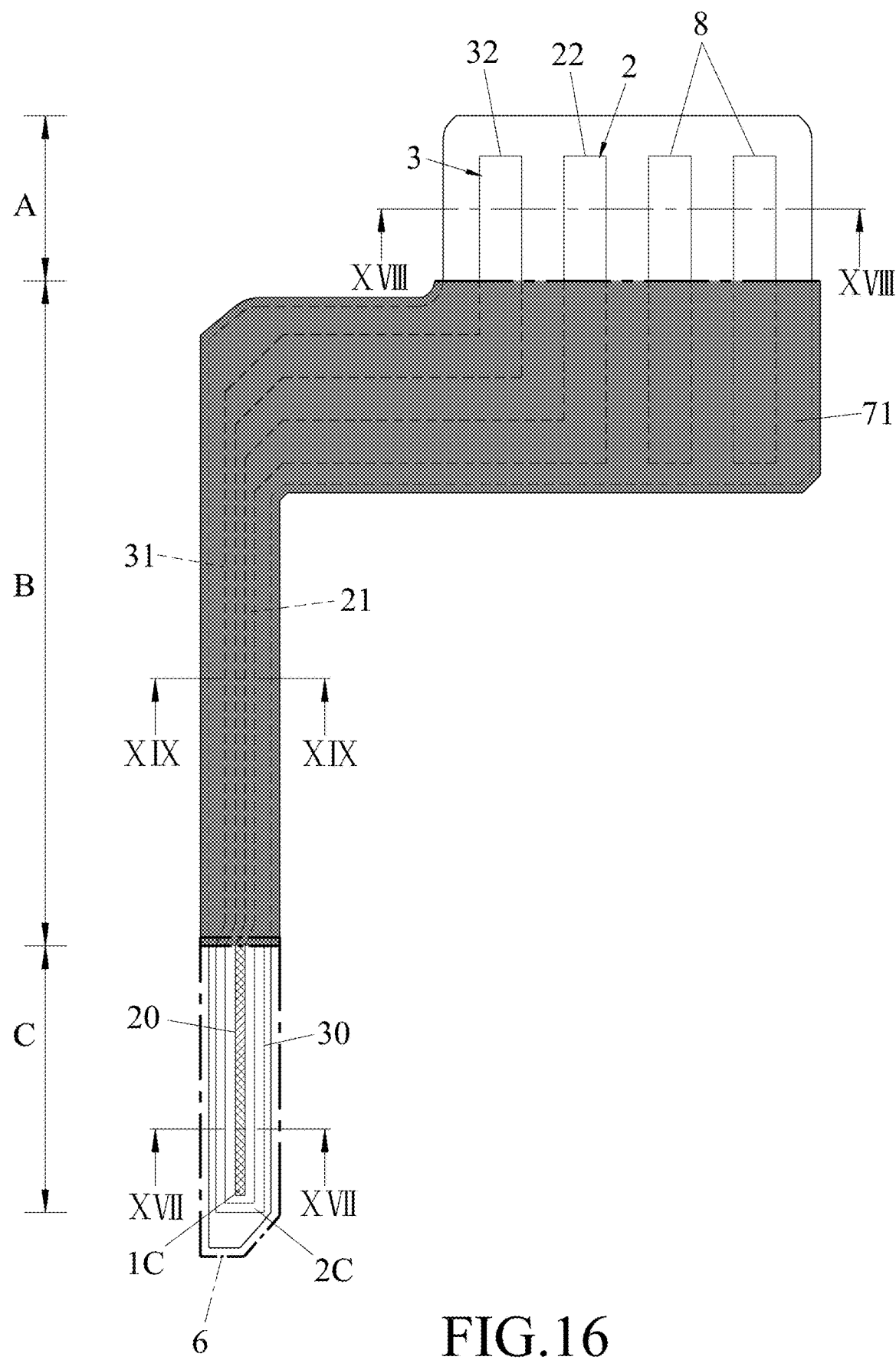
FIG. 16 is a schematic view illustrating a configuration of Embodiment 2 of the implantable micro-biosensor according to the disclosure.
Figure 17:
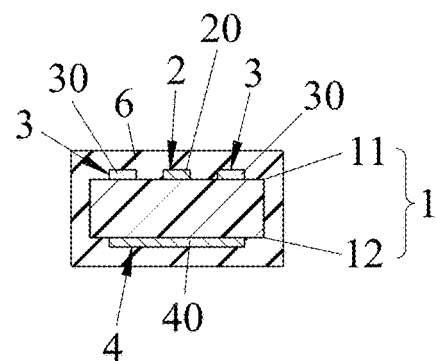
FIG. 17 is a schematic sectional view taken along line XVII-XVII of FIG. 16.
Figure 18:
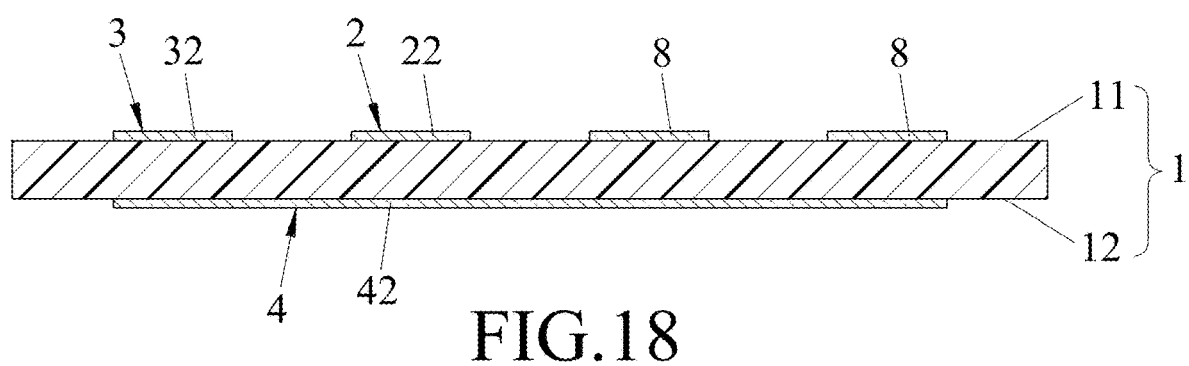
FIG. 18 is a schematic sectional view taken along line XVIII-XVIII of FIG. 16.
Figure 19:
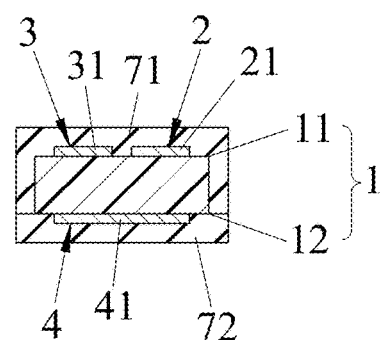
FIG. 19 is a schematic sectional view taken along line XIX-XIX of FIG. 16.

Referring to FIGS. 13 to 15, in yet another variation of Embodiment 1, the first conductive material 2C may cover whole of the second conductive material 2C, such that each of the first sensing section 20, the first connecting section 21, and the first signal output section 22 has a two-layered configuration which includes a layer of the second conductive material 2C and a layer of the first conductive material 1C covering the layer of the second conductive material 2C. The second working electrode 3 only includes a layer of the second conductive material 2C, as described above. Alternatively, it should be understood that the first working electrode 2 may only include the first conductive material 1C without the second conductive material 2C.

The positions and the areas of the first signal output region (A), the first signal connecting region (B), and the first sensing region (C) may be defined by an insulation layer. Therefore, in certain embodiments, sub-step (b) may be followed by a sub-step (b') of forming the first insulation layer 71 on the first surface 11 of the substrate 1 so as to define the first signal connecting region (B), at which the first insulation layer 71 is located, the first sensing region (C), which is not covered by the first insulation layer 71 and which is to be implanted under the skin of the body, and the first signal output region (A), which is not covered by the first insulation layer 71 and which is to be connected to the transmitter. At the first signal connecting region (B), each of the first connecting section 21 of the first working electrode 2 and the second connecting section 31 of the second working electrode 3 has a layered configuration which at least includes a layer of the second conducive material 2C.

In certain embodiment, sub-step (b) is performed to allow the second sensing section 30 to be spaced apart from the at least one side of the first sensing section 20 by a distance of up to 0.2 mm.

In certain embodiments, sub-step (a) is implemented by a screen printing process. Sub-step (b) is implemented by an etching process, and preferably a laser engraving process. Sub-step (d) is implemented with a conductive material by a sputtering process, but preferably a plating process.

Step (E) is implemented by immersing the substrate 1 formed with the first working electrode 2, the second working electrodes 3 and the counter electrode 4 into a solution containing the chemical reagent, so as to permit the first conductive material 1C of the first sensing section 20, the second conductive material 2C of the second sensing section 30 and the third sensing section 40 of the counter electrode 4 to be covered simultaneously with the chemical agent.

In certain embodiments, before step (E), step (D') is implemented by forming a third electrode (not shown) on the substrate 1. The third electrode is spaced apart from the counter electrode 4 and the first working electrode 2, and may be a reference electrode or a third working electrode.

In certain embodiments, step (E) may be followed by step (D") of forming the second insulation layer 72 on the second surface 12 of the substrate 1, so as to define the second sensing region (F) on the second surface 12 of the substrate 1.

It should be understood that the process for manufacturing Embodiment 1 of the implantable micro-biosensor according to the disclosure is not limited to the aforesaid steps, sub-steps, and order, and that the order of the aforesaid steps and sub-steps may be adjusted according to practical requirements.

In the process for manufacturing Embodiment 1 of the implantable micro-biosensor according to the disclosure, two sensing sections having different materials on the surfaces thereof may be formed on a same sensing region, such that the sensing sections can be covered simultaneously with a same chemical agent layer so as to simplify the conventional process. In addition, the geometries and sizes of the first and second working electrodes 2, 3, and the clearance between the first and second working electrodes 2, 3, and the like, can be controlled precisely by the patterning process. Furthermore, the processing performed on the second surface 12 of the substrate 1 may be modified according to practical requirements.

Embodiment 2

Referring to FIGS. 16 to 19, Embodiment 2 of the implantable micro-biosensor according to the disclosure is substantially similar to Embodiment 1 except for the following differences.

Figure 20:
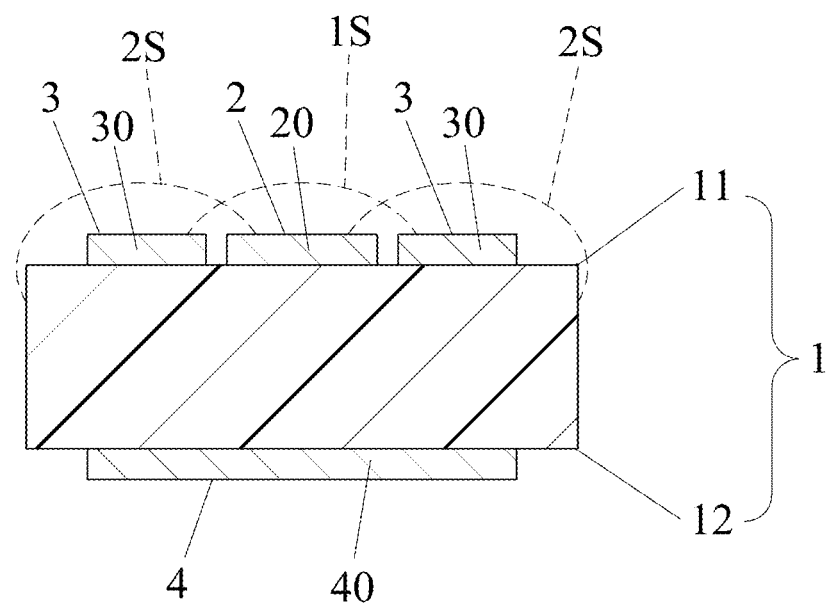
FIG. 20 is a schematic section view illustrating an interaction between one first sensing section and two second sensing sections of Embodiment 2.

In order to effectively reduce the interference of the interfering substance on the measurement of the physiological signal so as to be in an acceptable error range, in Embodiment 2, the second sensing section 30 is disposed along and spaced apart from at least three sides of the first sensing section 20 by a distance. In other words, the at least three sides of the first sensing section 20 are surrounded by and spaced apart from the second sensing section 30 by the distance. In certain embodiments, the distance is up to 0.2 mm. In certain embodiments, the distance ranges from 0.02 mm to 0.05 mm. Specifically, the second sensing section 30 is disposed in a U-shaped geometry along and spaced apart from the at least three sides of the first sensing section 20. Therefore, referring to FIG. 20, the second sensing section 30 forms at least two of the interference-eliminating regions 2S, which are located at two opposite sides of the first sensing section 20, and which overlap with the measuring region 1S, so as to not only consume the interfering substance approaching the second sensing section 30 but also consume the interfering substance within the first sensing section 20. In certain embodiments, the acceptable error range of the interference is up to 20%, for example, up to 10%.

A process for manufacturing Embodiment 2 is substantially similar to that for manufacturing Embodiment 1 except for the following differences.

In sub-step (b), the second conductive material 2C is patterned to permit the second conductive material 2C at the second area to be formed as a U-shaped geometry and to surround the second conductive material 2C at the first area. Therefore, the geometry of the second sensing section 30 and the extension of the second sensing section 30 to surround the first sensing section 20 may be modified by patterning the second conductive material 2C.

Figure 21:
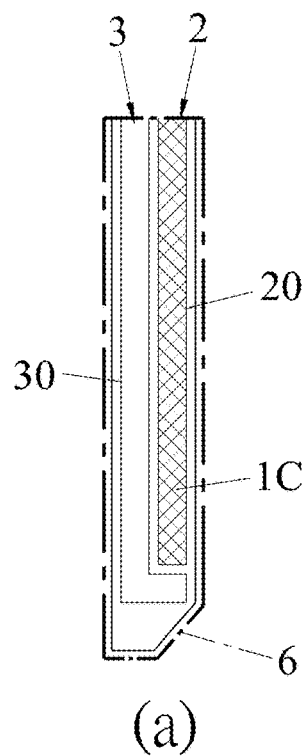
FIG. 21 shows fragmentary schematic views illustrating variations of a configuration of a first sensing section of a first working electrode and a second sensing section of a second working electrode of Embodiment 2.
Figure 21:
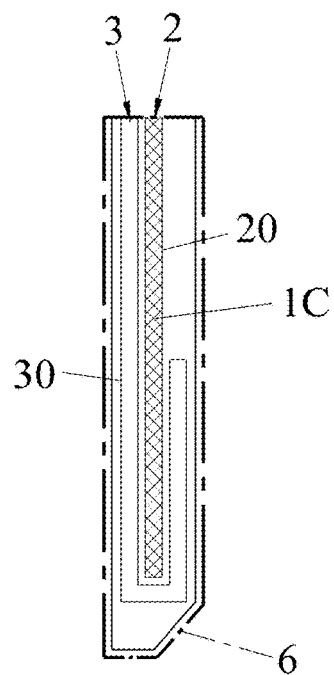

In addition, in other variations of Embodiment 2, the first and second sensing sections 20, 30 may be positioned as shown in FIG. 21(a) and FIG. 21(b). In other words, when the second sensing section 30 extends along and is spaced part from at least a portion of a periphery of the first sensing section 20, a ratio of the portion of the periphery of the first sensing section 20 to a total periphery of the first sensing section 20 ranges from 30% to 100%, such that the second sensing section 30 may be configured as an I-shaped (as illustrated in Embodiment 1), L-shaped, or U-shaped geometry.

Figure 22:
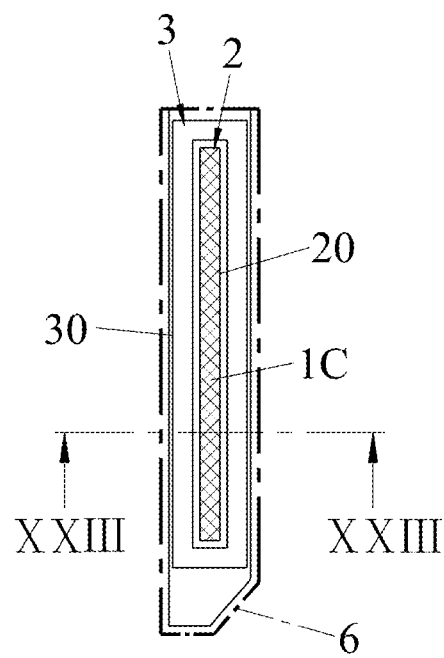
FIG. 22 is a fragmentary schematic view illustrating another variation of the configuration of the first sensing section of the first working electrode and the second sensing section of the second working electrode of Embodiment 2.
Figure 23:
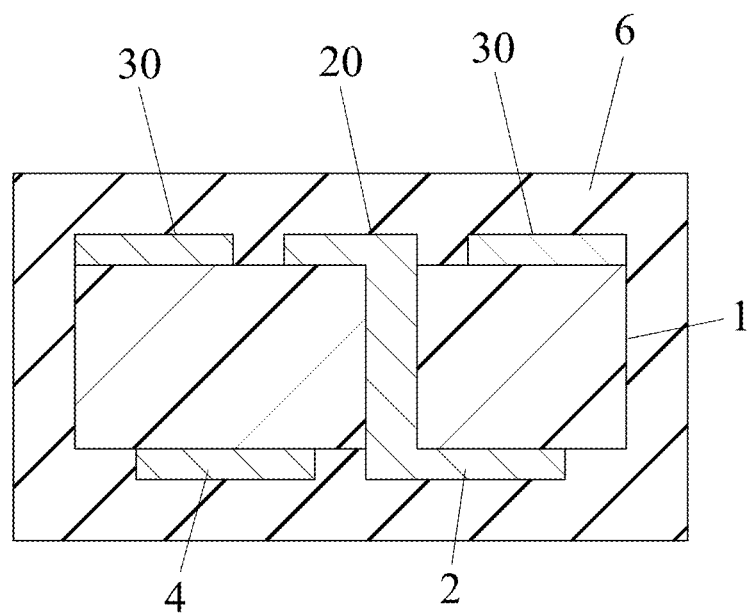
FIG. 23 is a schematic sectional view taken along along line XXIII-XXIII of FIG. 22.

Referring to FIGS. 22 and 23, in yet another variation of Embodiment 2, the second sensing section 30 may extend along and is spaced apart from whole of the periphery of the first sensing section 20. Specifically, the first connecting section 21 and the first output section 22 are disposed on the second surface 12 of the substrate 1. The first sensing section 20 includes a first portion disposed on the first surface 11 of the substrate 1, a second portion disposed on the second surface 12 of the substrate 1 and extending toward the first connecting section 21, and a middle portion extending through the substrate 1 to interconnect the first and second portions.

Embodiment 3

Figure 24:
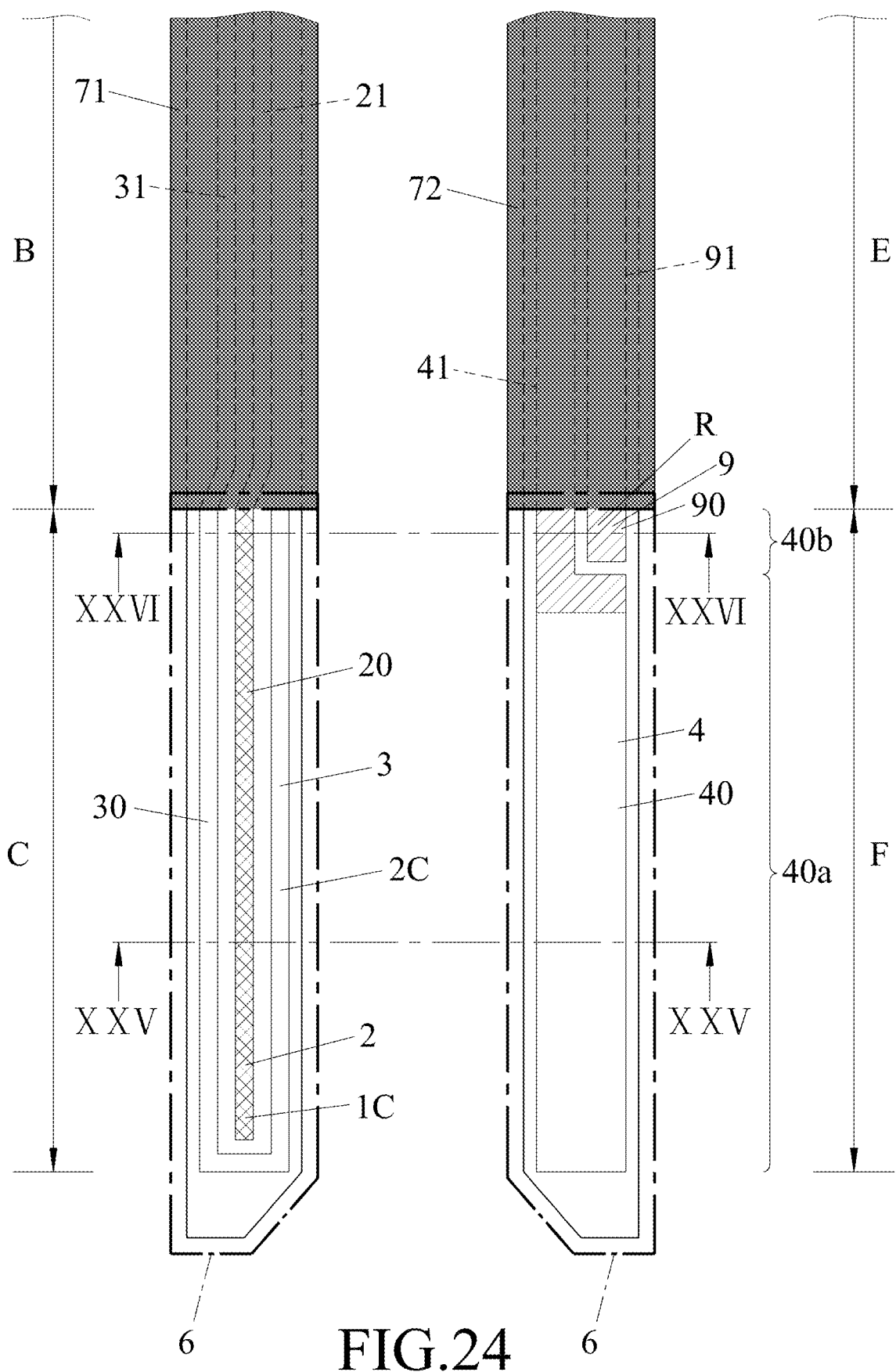
FIG. 24 shows fragmentary schematic views illustrating a configuration of Embodiment 3 of the implantable micro-biosensor according to the disclosure.
Figure 25:
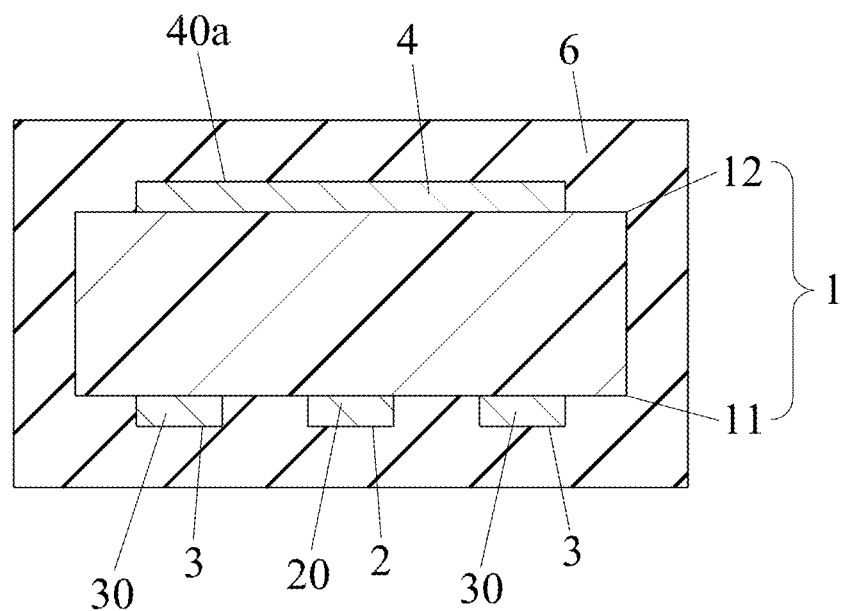
FIG. 25 is a schematic sectional view taken along line XXV-XXV of FIG. 24.
Figure 26:
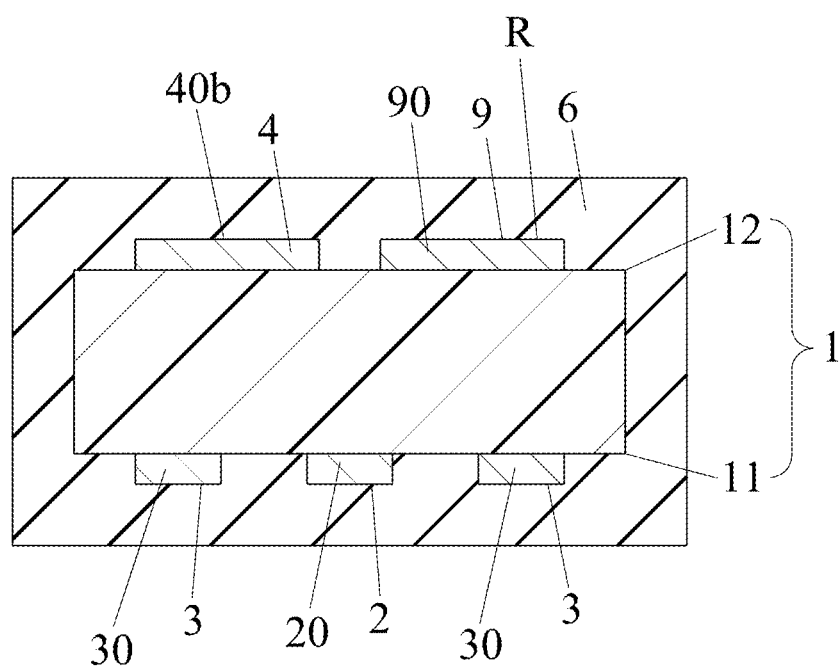
FIG. 26 is a schematic sectional view taken along line XXVI-XXVI of FIG. 24.

Referring to FIGS. 24 to 26, Embodiment 3 of the implantable micro-biosensor according to the disclosure is substantially similar to Embodiment 2 except for the following differences.

In Embodiment 3, the implantable micro-biosensor further includes a reference electrode 9 disposed on the second surface 12 of the substrate 1 and spaced from the counter electrode 4. A surface material of the reference electrode 9 at least includes the silver/silver halide (R). The reference electrode 9 has an area less than that of the counter electrode 4, so as to provide a sufficient capacity and to adjust the amount of the silver/silver halide (R).

Specifically, the counter electrode 4 is disposed on the second surface 12 of the substrate 1, and the third sensing section 40 of the counter electrode 4 includes a front portion 40a extending longitudinally along the second sensing region (F) and a rear portion 40b extending longitudinally toward a direction away from the second sensing region (F). In Embodiment 3, the third sensing section 40 of the counter electrode 4 is composed of the front and rear portions 40a, 40b. The reference electrode 9 is spaced apart from the counter electrode 4, and includes the fourth sensing section 90 located at the second sensing region (F). The fourth sensing section 90 has an area less than that of the third sensing section 40. Specifically, the front and rear portions 40a, 40b of the third sensing section 40 are disposed proximate to two adjacent sides of the fourth sensing section 90 of the reference electrode 9 to permit the counter electrode 4 to be configured as an L-shaped geometry. A total of the widths of the fourth sensing section 90 and the rear portion 40b of the counter electrode 4 is less than that of the front portion 40a of the counter electrode 4. In addition, the first and second insulation layers 71, 72 may have same lengths. Referring specifically to FIG. 26, the chemical reagent layer 6 may cover the first, second, third, and fourth sensing sections 20, 30, 40, 90.

Figure 27:
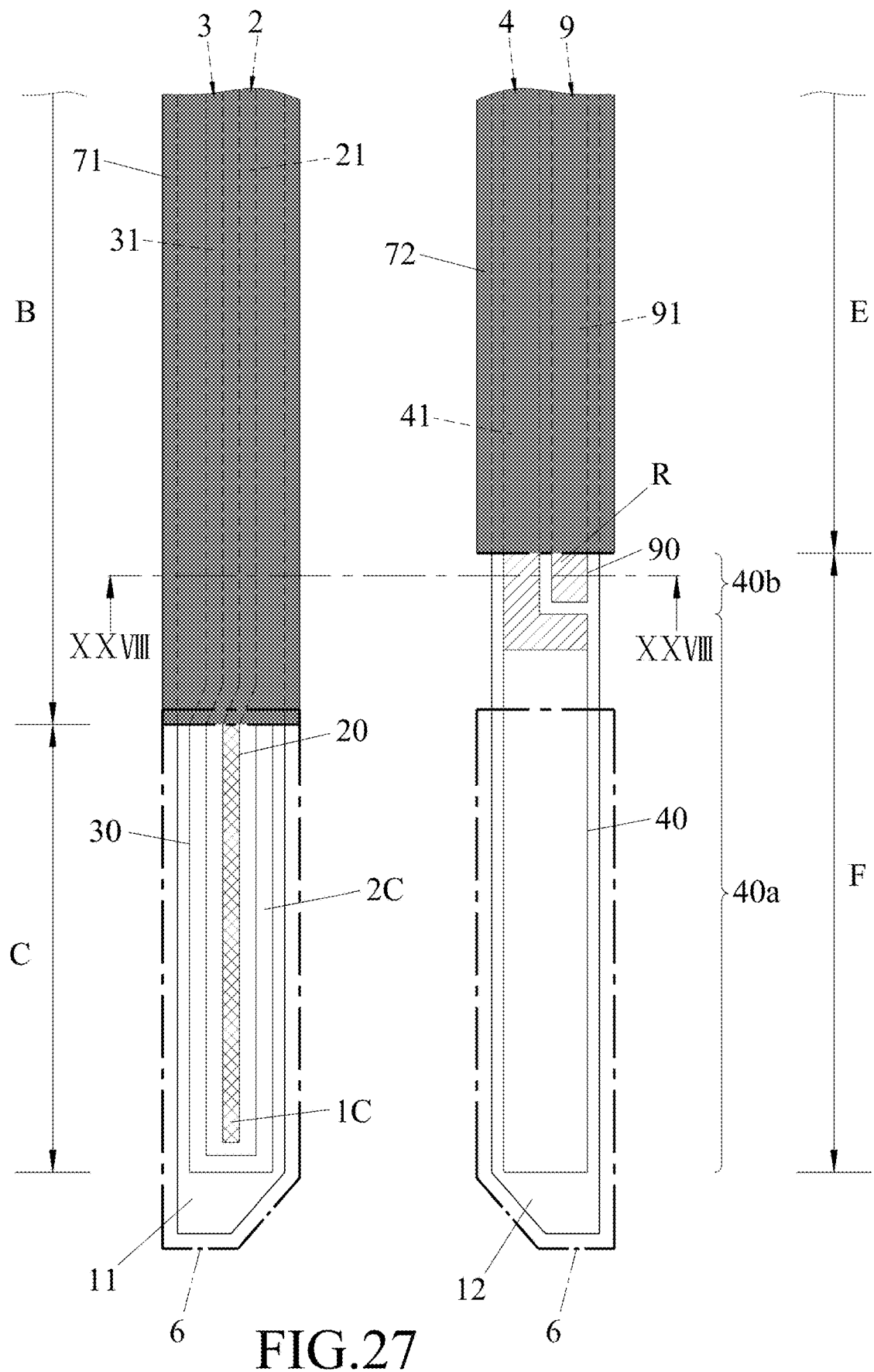
FIG. 27 shows fragmentary schematic views illustrating a variation of the configuration of Embodiment 3.
Figure 28:
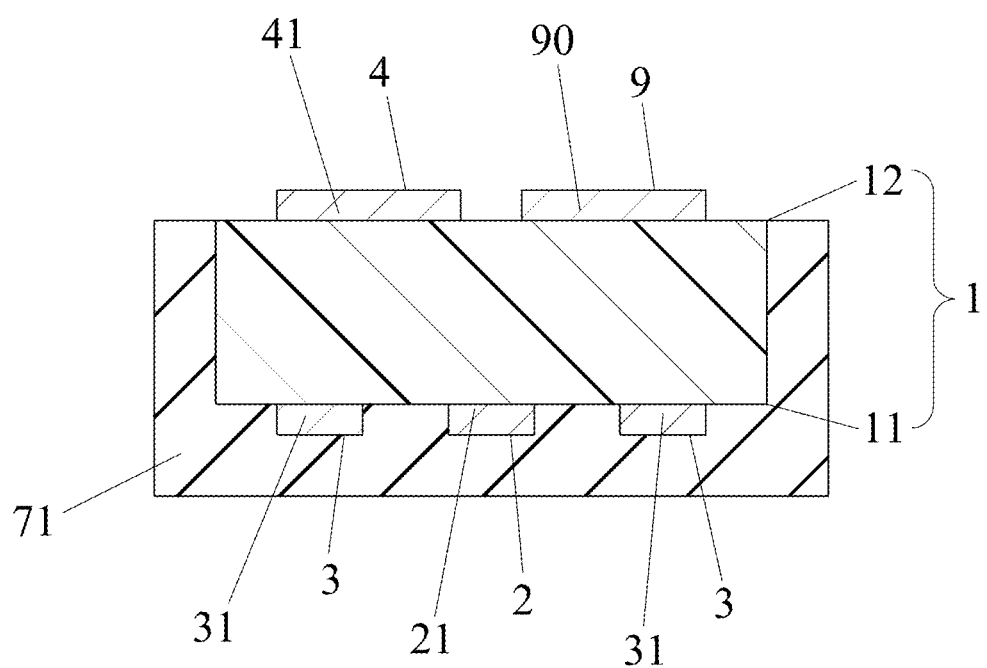
FIG. 28 is a schematic sectional view taken along line XXVIII-XXVIII of FIG. 27.

Referring to FIGS. 27 and 28, in a variation of Embodiment 3, the first and second insulation layers have different lengths such that the first sensing region (C) has a length less than that of the second sensing region (F). Therefore, the chemical reagent layer 6 only covers the first sensing section 20, the second sensing section 30, and the front portion 40a of the counter electrode 4. The fourth sensing section 90 of the reference electrode 9 may not be covered with the chemical reagent layer 6.

In another variation of Embodiment 3, at least a portion of the silver/silver halide (R) on the fourth sensing section 90 of the reference electrode 9 may be covered by the third conductive material 3C, so as to decrease the exposure area of the silver halide, thereby reducing the possibility of the silver halide being lost due to dissociation. Therefore, the side edge and/or the surface of the reference electrode 9 which is not covered by the third conductive material 3C may cooperate with the first working electrode 2 and the counter electrode 4 to conduct the measurement. In certain embodiments, the third conductive material 3C is carbon.

A process for manufacturing Embodiment 3 of the implantable micro-biosensor according to the disclosure is substantially similar to the process for manufacturing Embodiment 2 except for the following differences.

In step (D), the counter electrode 4 is formed on the second surface 12 of the substrate 1, and includes the third sensing section 40 located at the second sensing region (F). The third sensing section 40 includes the front portion 40a and the rear portion 40b. In step (D'), the reference electrode 9 is formed on the second surface 12 of the substrate 1, and is spaced apart from the counter electrode 4. The reference electrode 9 includes the fourth sensing section 90 located at the second sensing region (F).

It is noted that, before the micro-biosensor is ready for shipping out of the plant for sale, the counter electrode 4 of Embodiment 1 or 2, or the reference electrode 9 of Embodiment 3 can have no silver halide (that is, the initial amount of the silver halide can be zero) but silver. An initial amount of the silver halide can be generated on the counter electrode 4 or the reference electrode 9 by oxidizing the silver coated on the counter electrode 4 or the reference electrode 9 during a very first replenishment period after the micro-biosensor is implanted subcutaneously into the patient and before a first measurement is proceeded. In such case, the silver is oxidized to silver ion thus to be combined with chloride ion in the body fluid to form the silver halide. The measurement can be performed after a predetermined ratio between silver and silver halide is reached.

Figure 29:
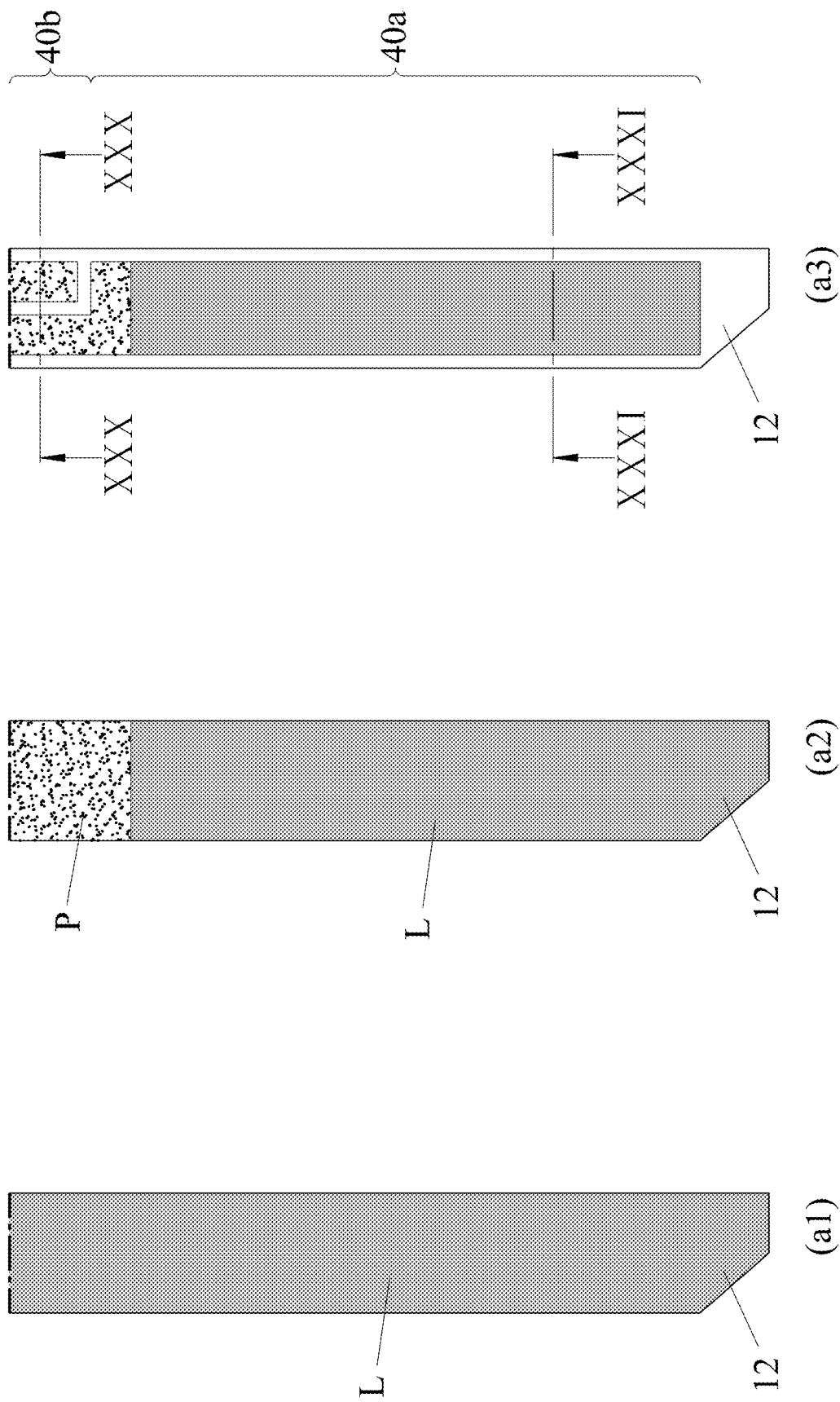
FIG. 29 shows schematic views illustrating steps (a1), (a2), (a3) of a process for manufacturing Embodiment 3.

Accordingly, referring to FIG. 29, in a first process for manufacturing Embodiment 3 of the implantable micro-biosensor, steps (D) and (D') are implemented by the sub-steps of:

(a1) forming a backing material layer (L) on the second surface 12 of the substrate 1; and (a2) applying a reference electrode material (for example, silver-silver halide) or a precursor material (P) (for example, silver) of the reference electrode material on a portion of the backing material layer (L);

(a3) subjecting the backing material layer (L) and the reference electrode material or the precursor material (P) to patterning so as to define a third area and a fourth area which are separated from each other and which are not connected electrically to each other, the backing material layer (L) at the third area being configured as the counter electrode 4.

Specifically, the active area of the counter electrode 4 and the reference electrode 9, the cooperated configuration between the above two, the location or size of the silver-silver halide on the surface of the electrode can be easily controlled through sub-step (a2) so as to complete the manufacture of the counter electrode 4 and the reference electrode 9 and control the amount of the silver-silver halide.

Figure 30:
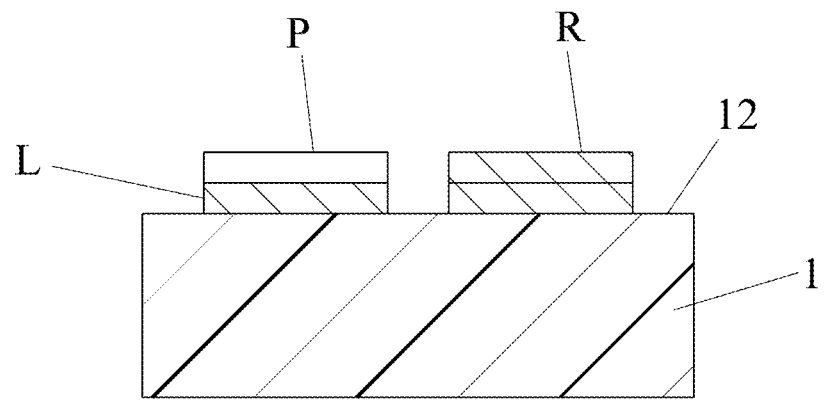
FIG. 30 is a schematic sectional view taken along line XXX-XXX of FIG. 29 for showing the configuration of a second surface of Embodiment 3.
Figure 31:
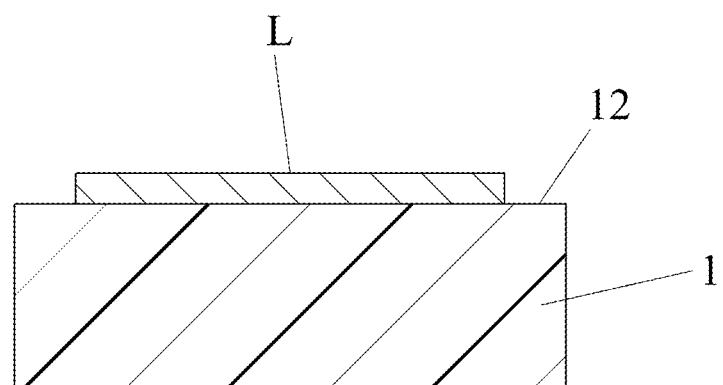
FIG. 31 is a schematic sectional view taken along line XXXI-XXXI of FIG. 29 for showing the configuration of the second surface of Embodiment 3.

Specifically, the backing material layer (L) located at the third area has a different width along a longitudinal direction of the third area. A front portion of the backing material layer (L) having a greater width is used for forming the front portion 40a of the third sensing section 40 of the counter electrode 4, and a rear portion of the backing material layer (L) having a smaller width is used for forming the rear portion 40b of the third sensing section 40 of the counter electrode 4. A portion or whole of the reference electrode material or the precursor material (P) is located at the fourth area. If the reference electrode material is applied in sub-step (a2), the fourth sensing section 90 of the reference electrode 9 is formed directly thereby. Alternatively, if the precursor material (P) is applied in sub-step (a2), an additional sub-step (a4) is implemented to convert the precursor material (P) at the fourth area to the reference electrode material to form the fourth sensing section 90 of the reference electrode 9. Referring specifically to FIGS. 30 and 31, the rear portion 40b of the third sensing section 40 of the counter electrode 4 is formed as a laminated configuration which includes the backing material layer (L) and a layer of the precursor material (P) covering the backing material layer (L). The fourth sensing section 90 of the reference electrode 9 is formed as a laminated configuration which includes the backing material layer (L) and a layer of the silver/silver halide (R) covering the backing material layer (L). The front portion 40a of the third sensing section 40 of the counter electrode 4 is formed as a single-layered configuration made of the backing material layer (L).

In Embodiment 3, a portion of the precursor material (P) is located at the fourth area, and a remaining portion of the precursor material (P) is located at the third area. In another variation of Embodiment 3, in sub-step (a3), whole of the precursor material (P) may be located at the fourth area.

In a second process for manufacturing Embodiment 3 of the implantable micro-biosensor, steps (D) and (D') are implemented by the sub-steps of:

(b1) forming the backing material layer (L) on the second surface 12 of the substrate 1;

(b2) subjecting the backing material layer (L) to patterning to define a third area and a fourth area which are separated from each other and which are not connected electrically to each other, the backing material layer (L) at the third area being configured as the counter electrode 4; and (b3) applying the reference electrode material or the precursor material (P) of the reference electrode material to at least a portion of the fourth area, so as to permit the fourth area to be configured as the reference electrode 9.

If the reference electrode material is applied in sub-step (b3), the fourth sensing section 90 of the reference electrode 9 is formed directly thereby. Alternatively, if the precursor material (P) is applied in sub-step (b3), an additional sub-step (a4) is implemented to convert the precursor material (P) at the fourth area to the reference electrode material to form the fourth sensing section 90 of the reference electrode 9.

In certain embodiments, the backing material layer (L) may be formed as a single-layered configuration or a multi-layered configuration, each of which is made from carbon, silver, or a combination thereof. Specifically, the backing material layer (L) may be formed as a single-layered configuration made of carbon, such that the third sensing section 40 of the counter electrode 4 is configured as a carbon layer. Alternatively, the backing material layer (L) may be formed as a two-layered configuration, which includes a silver layer disposed on the second surface of the substrate 1 and a carbon layer disposed on the silver layer.

Embodiment 4

Figure 32:
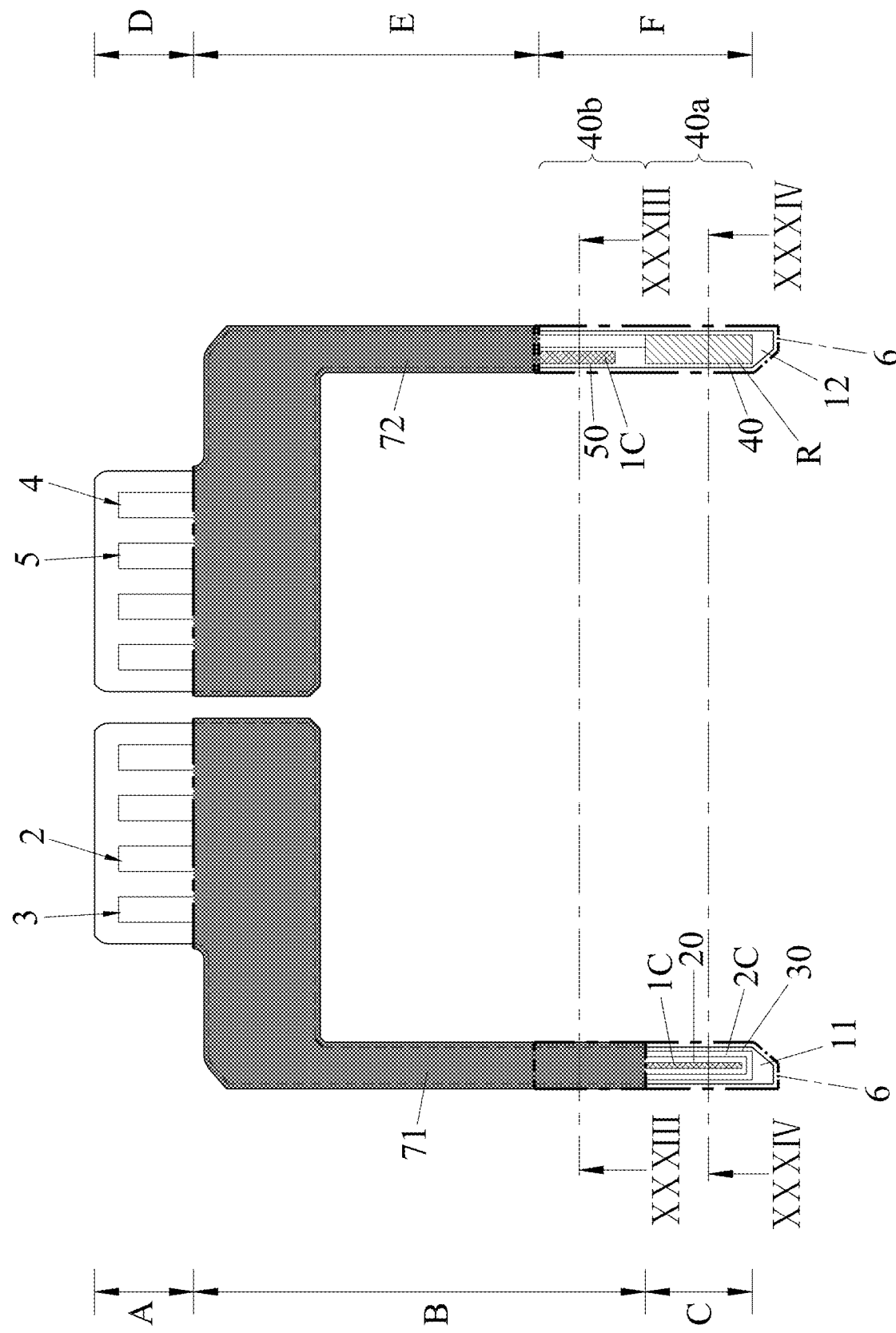
FIG. 32 shows schematic views illustrating a configuration of Embodiment 4 of the implantable micro-biosensor according to the disclosure.
Figure 33:
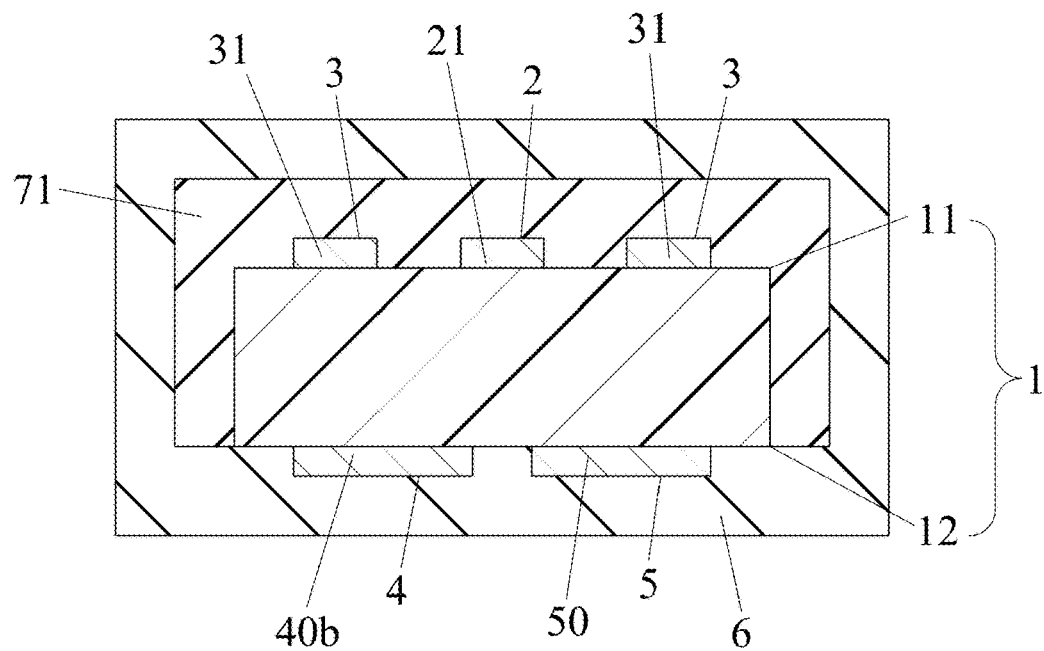
FIG. 33 is a schematic sectional view taken along line XXXIII-XXXIII of FIG. 32.
Figure 34:
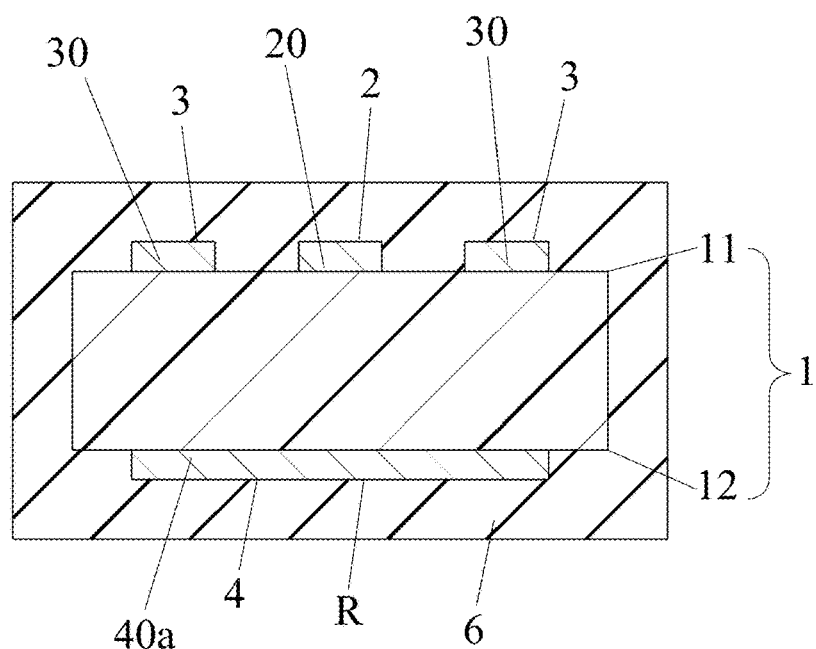
FIG. 34 is a schematic sectional view taken along line XXXIV-XXXIV of FIG. 32.

Referring to FIGS. 32 to 34, Embodiment 4 of the implantable micro-biosensor according to the disclosure is substantially similar to Embodiment 3 except for the following differences.

In Embodiment 4, the counter electrode 4 also functions as a reference electrode, and the reference electrode 9 in Embodiment 2 is replaced with a third working electrode 5. The material and configuration for the third working electrode 5 may be the same as those described above for the first working electrode 2 or the second working electrode 3. Specifically, the configuration of the third working electrode 5 in Embodiment 4 is the same as that of the first working electrode 2 in Embodiment 1, and includes a carbon layer and a platinum layer disposed on the carbon layer. In certain embodiments, the third working electrode 5 may be disposed on the first surface 11 of the substrate 1. In other words, the third working electrode 5 and the counter electrode 4 may be disposed on the same surface or different surfaces of the substrate 1. In addition, the configuration of the third working electrode 5 is not limited to Embodiment 4 and can be arranged as Embodiment 1 shown in FIG. 8, that is, the length, area and even shape of the third working electrode 5 can be the same as the counter electrode 4.

Referring specifically to FIGS. 33 and 34, a process for manufacturing Embodiment 4 of the implantable micro-biosensor according to the disclosure is substantially similar to the process for manufacturing Embodiment 3 except for the following differences.

In the process for manufacturing Embodiment 4, in step (D'), the third working electrode 5 is formed on the second surface 12 of the substrate 1, and is spaced apart from the counter electrode 4. The third working electrode 5 includes a fourth sensing section 50 located at the second sensing region (F). The fourth sensing section 50 is parallel to the rear portion 40b of the third sensing section 40, and is spaced apart from the front portion 40a of the third sensing section 40 along a longitudinal direction of the counter electrode 4. In other words, the counter electrode is configured as an L-shaped geometry, such that the third sensing section 40 of the counter electrode is spaced part from the fourth sensing section 50 of the third working electrode 5.

In certain embodiments, step (D) is implemented by the sub-steps of:

(c1) forming a backing material layer (L) on the second surface 12 of the substrate 1;

(c2) defining on the second surface 12 of the substrate 1, a third area and a fourth area which are separated from each other, the third area being used for the counter electrode 4, and the backing material layer (L) located at the third area has a different width along a longitudinal direction of the third area. A front portion of the backing material layer (L) having a greater width is used for forming the front portion 40a of the third sensing section 40 of the counter electrode 4, and a rear portion of the backing material layer (L) having a smaller width is used for forming the rear portion 40b of the third sensing section 40 of the counter electrode 4; and (c3) applying the reference electrode material (for example, silver-silver halide) or the precursor material (P) (for example, silver) of the reference electrode material on at least a portion of the backing material layer (L) at the third area, and specifically, at the front portion 40a of the third sensing section 40.

If the precursor material (P) is applied in sub-step (c3), an additional sub-step (c4) is implemented to convert the precursor material (P) to the reference electrode material, so as to permit the front portion 40a of the counter electrode 4 to be used as the third sensing section 40 and to function as a reference electrode as well.

In certain embodiments, in sub-step (c1), the backing material layer (L) may be formed as a single-layered configuration or a multi-layered configuration, each of which is made from carbon, silver, or a combination thereof.

It should be understood that the counter electrode 4 may be formed as a single-, double-, or triple-layered configuration. The counter electrode 4 formed as a double-layered configuration may include a conductive material layer (for example, a carbon layer, but is not limited thereto) disposed on the substrate 1, and a layer of the silver/silver halide (R) covering the conductive material layer. The conductive material layer is provided to avoid impedance problem due to excessive halogenation of silver in sub-step (c4) or the abovementioned initial halogenation step.

When the conductive material layer is a carbon layer, another conductive material layer (for example, a silver layer) may be disposed between the second surface 12 of the substrate 1 and the conductive material layer to permit the counter electrode 4 to be formed as a triple-layered configuration, so as to reduce the high impedance problem which may occur at the second signal output region (D) when the carbon layer is disposed directly on the second surface 12 of the substrate 1.

In certain embodiments, the counter electrode 4 may be formed as a single-layered configuration. Therefore, the backing material layer (L) in sub-step (c1) may be made from the silver/silver halide, a mixture of the silver/silver halide and a conductive material (for example, carbon), or a mixture of silver and the conductive material (for example, carbon), and sub-step (c3) may be omitted. The counter electrode 4 is thus formed as a single-layered configuration including silver/silver halide or the mixture of the silver/silver halide and the conductive material (for example, carbon). The amount of the silver/silver halide present in the counter electrode 4 is not specifically limited as long as the counter electrode 4 executes the intended operation. Formation of the counter electrode 4 using the mixture of the silver/silver halide and the conductive material may alleviate the insulation problem during halogenation, the adhesion problem during lamination, and the high impedance problem of the second signal output region (D).

Similarly, in Embodiment 4, the first working electrode 2 is used for measuring the physiological signal, and the second working electrode 3 is used to reduce the interference of the interfering substance in the body to the measurement. However, regeneration of silver halide is carried out by cooperation of the third working electrode 5 with the counter electrode 4. Specifically, the third potential difference is applied between the counter electrode 4 and the third working electrode 5 to permit the counter electrode 4 to have a potential higher than that of the third working electrode 5, so as to permit the counter electrode 4 to perform an oxidation reaction to regenerate the silver halide, thereby enhancing the efficiency of the measurement, the consumption of the interference, and the regeneration of silver halide.

Embodiment 5

Figure 35:
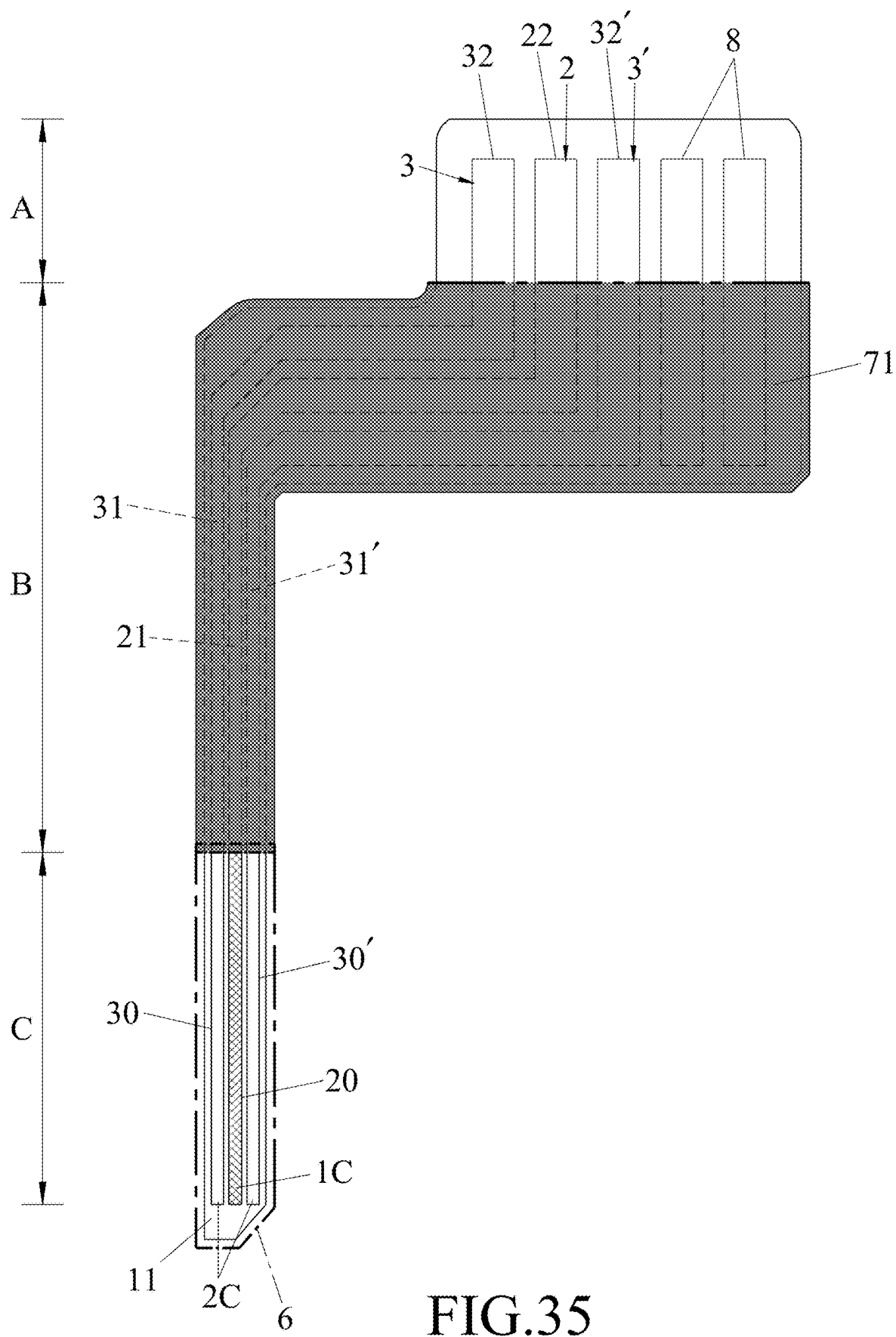
FIG. 35 is a schematic view illustrating a configuration of Embodiment 5 of the implantable micro-biosensor according to the disclosure.

Referring to FIG. 35, Embodiment 5 of the implantable micro-biosensor according to the disclosure is substantially similar to Embodiment 1 except for the following differences.

In Embodiment 5, two of the second working electrodes 3, 3' are included. Similar to the second working electrode 3 described above, the second working electrode 3' includes a second sensing section 30', a second connecting section 31', and a second output section 32'. The second sensing sections 30, 30' of the second working electrodes 3, 3' may have the same or different lengths and/or areas. A distance between one of the two second sensing sections 30, 30' and the first sensing section 20 may be different from that between the other one of the two second sensing sections 30, 30' and the first sensing section 20.

A process for manufacturing Embodiment 5 of the implantable micro-biosensor according to the disclosure is substantially similar to the process for manufacturing Embodiment 1 except for the following differences.

In the process for manufacturing Embodiment 5 of the implantable micro-biosensor according to the disclosure, in sub-step (b), two of the second areas are formed to define the two second working electrodes 3, 3', and the two second sensing sections 30, 30' of the two second working electrodes 3, 3' are disposed, respectively, along two opposite sides of the first sensing section 20 of the first working electrode 2.

Operation Procedures of Implantable Micro-Biosensor:

Application Embodiment 1

Embodiment 4 of the implantable micro-biosensor according to the disclosure is used in Application Embodiment 1, and includes the substrate 1, the first working electrode 2, the second working electrode 3, the counter electrode 4, the third working electrode 5, and the chemical reagent layer 6. The first sensing section 20 of the first working electrode 2 includes a carbon layer, and a platinum layer covering the carbon layer. The second sensing section 30 of the second working electrode 3 is formed as a U-shaped geometry and surrounds around the first sensing section 20, and includes a carbon layer. The third sensing section 40 of the counter electrode 4 includes a carbon layer and a silver/silver chloride layer covering the carbon layer. The fourth sensing section 50 of the third working electrode 5 has a configuration which is the same as that of the first sensing section 20 of the first working electrode 2. The chemical reagent layer 6 covers the first, second, third, fourth sensing sections 20, 30, 40, 50.

Referring to FIGS. 36 to 39, Embodiment 4 of the the implantable micro-biosensor according to the disclosure is used for detecting a physiological parameter (for example, a concentration) of an analyte (for example, glucose) in a body during a detecting time period (T) that includes at least one first time section (T1) for measuring the analyte, at least one second time section (T2) for consuming an interfering substance in the body, and at least one third time section (T3) for regenerating silver chloride.

During the first time section (T1), switch S1 is switched to a close-circuit state and the first potential difference (for example, 0.5 V, but is not limited thereto) is applied between the first working electrode 2 and the counter electrode 4 to permit the first working electrode 2 to have a potential V1 higher than a potential V4 of the counter electrode 4, so as to permit the first working electrode 2 to perform the aforesaid oxidation reaction and to perform the electrochemical reaction with the chemical reagent layer 6 and the analyte to obtain the physiological signal (i1). At the same time, the counter electrode 4 carries out a reduction reaction to reduce silver chloride to silver according to an equation below.

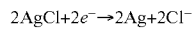

$$2AgCl + 2e^- \rightarrow 2Ag + 2Cl^-$$

In addition, a value of the first time section (T1) can be a constant, such as 2.5 seconds, 5 seconds, 15 seconds, 30 seconds, 1 minute, 2.5 minutes, 5 minutes, 10 minutes or 30 minutes. Preferably, the value of the first time section (T1) is 30 seconds.

During the second time section (T2), switch S2 is switched to a close-circuit state and the second potential difference (for example, 0.5 V, but is not limited thereto) is applied between the second working electrode 3 and the counter electrode 4 to permit the second working electrode 3 to have a potential V2 higher than the potential V4 of the counter electrode 4, so as to permit the second working electrode 3 to perform a reaction on the surface thereof, thereby consuming the interfering substance.

During the third time section (T3), switch S3 is switched to a close-circuit state and the third potential difference is applied between the counter electrode 4 and the third working electrode 5 to permit the potential V4 of the counter electrode 4 to be higher than a potential V3 of the third working electrode 5, so as to permit the counter electrode 4 to perform an oxidation reaction, thereby regenerating the silver chloride by oxidizing silver to silver ions, which is then combine with chloride ions in the biological fluid to form silver chloride.

The steps of obtaining the physiological signal, consuming the interfering substance, and regenerating the silver chloride may be implemented simultaneously or separately by proper arrangement of the potentials V1, V2, V3, V4 of the first, second, and third working electrodes 2, 3, 5 and the counter electrode 4, proper arrangement of the first, second, and third potential differences, and proper switching of switches S1, S2, S3. In other words, the first, second, and third time sections (T1, T2, T3) my partially or fully overlap with one another, or are free from overlapping with one another. In addition, each of the first, second, and third time sections (T1, T2, T3) may be a constant or variable time period.

Figure 36:
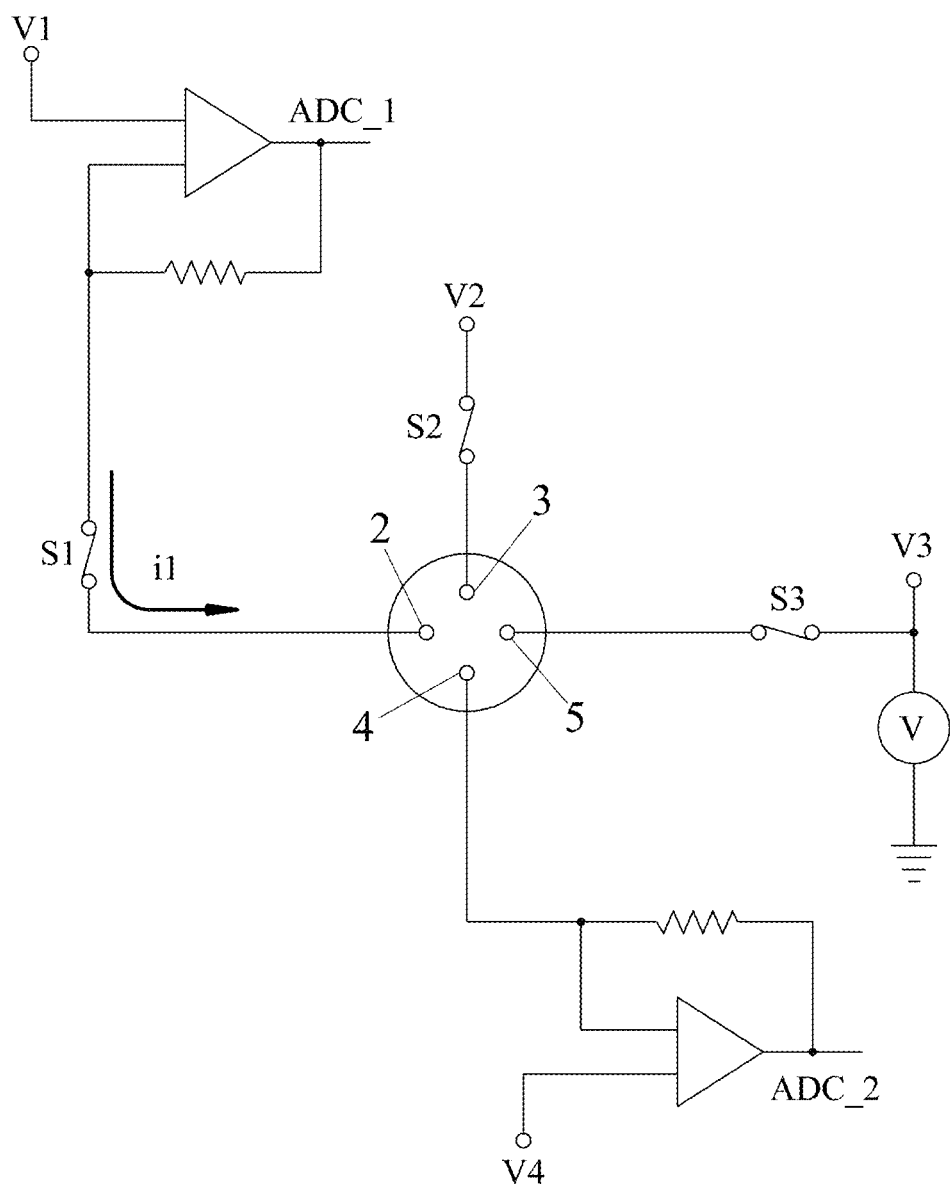
FIG. 36 is a circuit diagram illustrating a circuit design of Application Embodiment 1.
Figure 37:
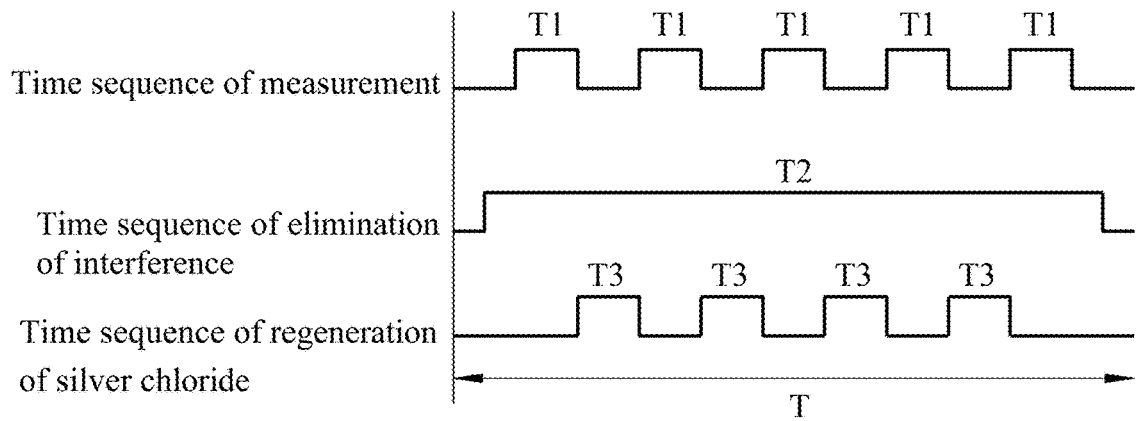
FIG. 37 is a schematic time-sequence diagram illustrating an operation time sequence of Application Embodiment 1.

Specifically, referring to FIGS. 36 and 37, the horizontal and vertical axles of the figures respectively represent time and current, in which the line of the measurement action shows the application and remove of the first potential difference, another line of the interference eliminating action shows the application and remove of the second potential difference, and further another line of the silver chloride regeneration action shows the application and remove of the third potential difference. The detecting time period (T) in Application Embodiment 1 includes five of the first time sections (T1), one of the second time section (T2), and four of the third time sections (T3). During the whole of the detecting time period (T), switch S2 is switched to a close-circuit state and the potential V2 of the second working electrode 3 is permitted to be higher than the potential V4 of the counter electrode 4, so as to permit the second working electrode 3 to perform consumption of the interference. During the detecting time period (T), switch S1 is switched cyclically and alternately between an open-circuit state and a close-circuit state, so as to permit the first working electrode 2 to cooperate intermittently with the counter electrode 4 to carry out the measurement of the analyte. Adjacent two of the first time sections (T1) may be separated from each other by implementing an open circuit operation or by applying a zero potential difference.

In addition, during a time interval (i.e., a corresponding one of the third time sections (T3)) between two adjacent ones of the first time sections (T1), the counter electrode 4 cooperates with the third working electrode 5 to execute the regeneration of the silver chloride. In other words, the first time sections (T1) and the third time sections (T3) do not overlap with each other.

Application Embodiment 2

Figure 38:
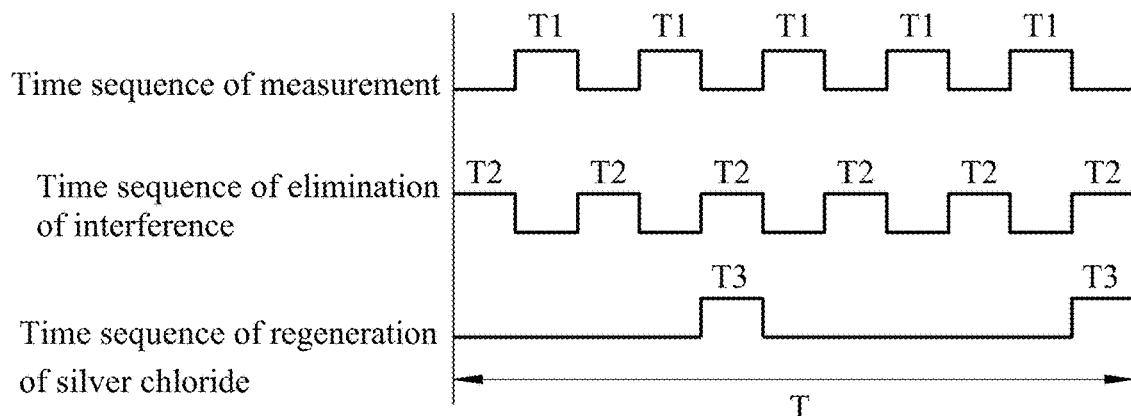
FIG. 38 is a schematic time-sequence diagram illustrating an operation time sequence of Application Embodiment 2.

Referring to FIG. 38, the operation procedures for Application Embodiment 2 are substantially similar to those of Application Embodiment 1 except for the following differences.

In Application Embodiment 2, the detecting time period (T) includes five of the first time section (T1), six of the second time sections (T2), and two of the third time sections (T3). The first time sections (T1) and the second time sections (T2) do not overlap with each other. That is to say, when the first working electrode 2 performs the measurement of the analyte during the first time sections (T1), the second working electrode 3 can be operated by implementing an open circuit or by grounding. In addition, the silver chloride regeneration action can be performed after several measurement actions or interference eliminating actions. For example, the two third time sections (T3) in Application Embodiment 2 only overlap with two of the second time sections (T2). That is to say, the silver chloride regeneration action is performed after two measurement actions and three interference eliminating actions. In addition, the first interference eliminating action may be carried out prior to the first measurement action so as to effectively avoid the interference of the interfering substance in the body to the measurement.

Application Embodiment 3

Figure 39:
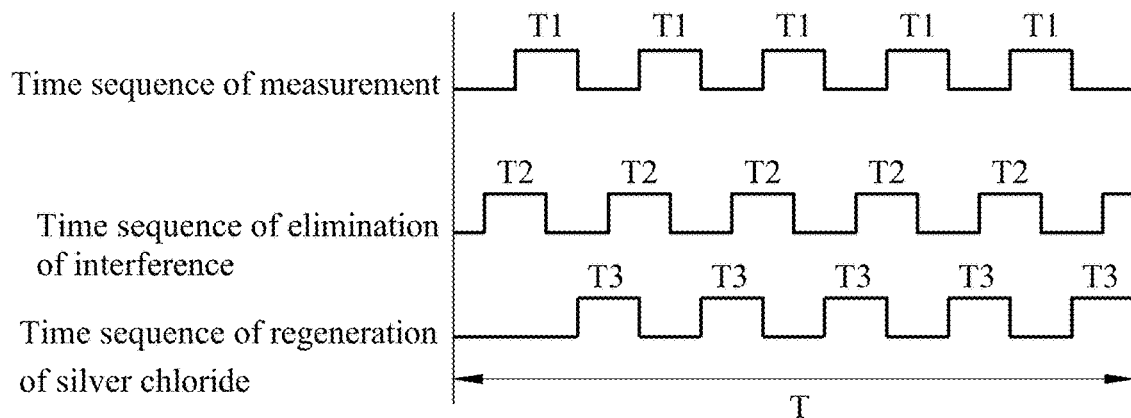
FIG. 39 is a schematic time-sequence diagram illustrating an operation time sequence of Application Embodiment 3.

Referring to FIG. 39, the operation procedures for Application Embodiment 3 are substantially similar to those of Application Embodiment 1 except for the following differences.

In Application Embodiment 3, the detecting time period (T) includes five of the first time sections (T1), six of the second time sections (T2), and five of the third time sections (T3). The first time sections (T1) and the second time sections (T2) partially overlap with each other. The second time sections (T2) and the third time sections (T3) partially overlap with each other. The first time sections (T1) and the third time sections (T3) do not overlap with each other. Similarly, the first interference eliminating action may be carried out prior to the first measurement action so as to effectively avoid the interference of the interfering substance to the measurement. Regeneration of the silver chloride may be performed during a time interval between two adjacent ones of the first time sections (T1), so as to permit an amount of silver halide present in the third sensing section 40 of the counter electrode 4 to be maintained in a safe range.

Application Embodiment 4

The procedures for Application Embodiment 4 are substantially similar to those of Application Embodiment 1 except for the following differences.

In Application Embodiment 4, Embodiment 2 of the implantable micro-biosensor according to the disclosure is used, and includes the substrate 1, the first working electrode 2, the second working electrode 3, the counter electrode 4, and the chemical reagent layer 6. The first sensing section 20 of the first working electrode 2 includes a carbon layer and a platinum layer covering the carbon layer. The second sensing section 30 of the second working electrode surrounds 3 is formed as a U-shaped geometry and surrounds the first sensing section 20, and includes a carbon layer. The third sensing section 40 of the counter electrode 4 includes a carbon layer and a silver/silver chloride layer covering the carbon layer. The chemical reagent layer 6 covers the first, second, and third sensing sections 20, 30, 40. Specifically, the third working electrode 5 is not included in Embodiment 2 of the implantable micro-biosensor.

Figure 40:
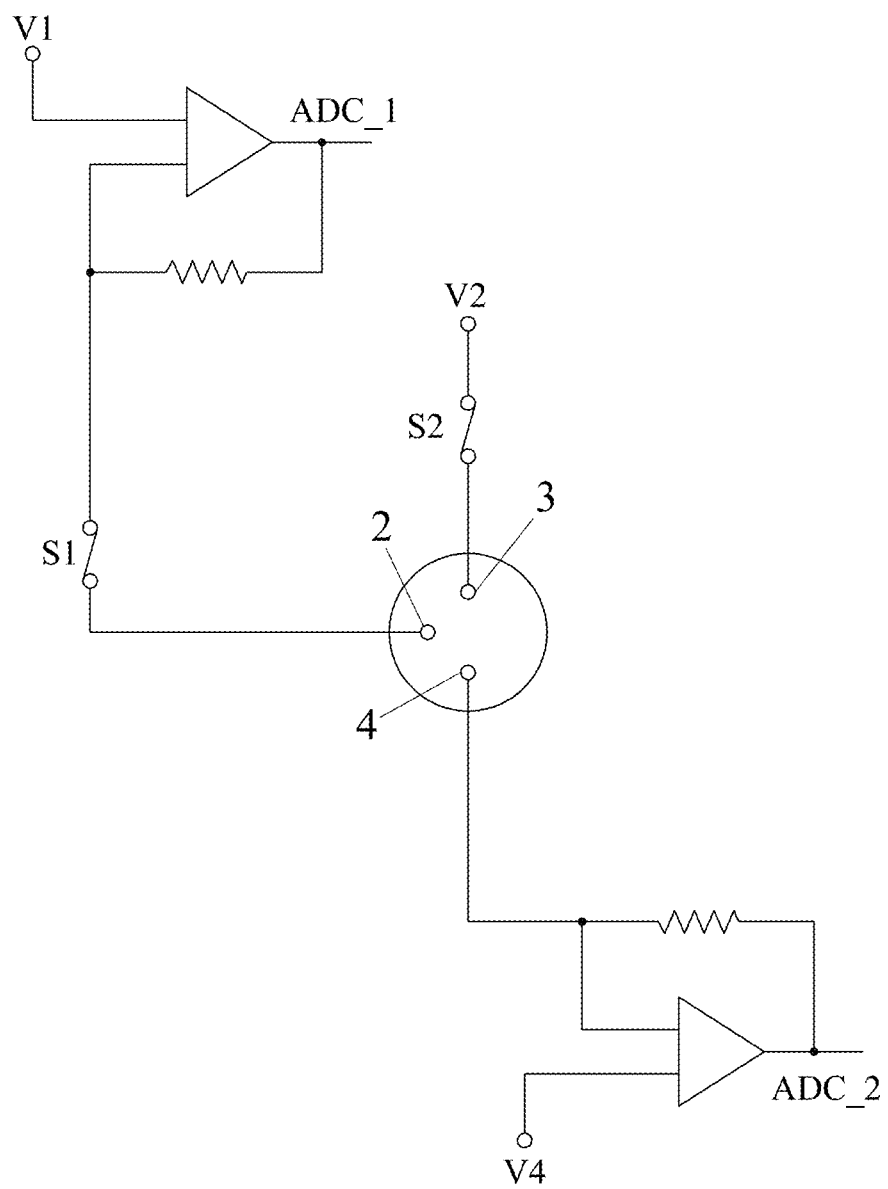
FIG. 40 is a circuit diagram illustrating a circuit design of Application Embodiment 4.

Referring to FIG. 40, the consumption of the interference is executed by applying the second potential difference between the second working electrode 3 and the counter electrode 4 to permit the potential V2 of the second working electrode 3 to be higher than the potential V4 of the counter electrode 4, and to permit the second working electrode 3 to perform an oxidation reaction to consume the interfering substance.

Regeneration of the silver chloride is executed by applying the third potential difference between the counter electrode 4 and the second working electrode 3 to permit the potential V4 of the counter electrode 4 to be higher than the potential V2 of the second working electrode 3, and to permit the counter electrode 4 to function as a working electrode to perform the oxidation reaction so as to regenerate silver chloride. Specifically, switch S2 may be selectively connected to a relatively high potential (i.e., a potential higher than the potential V4 of the counter electrode 4) to allow the second working electrode 3 to execute the consumption of the interference, or a relatively low potential (i.e., a potential lower than the potential V4 of the counter electrode 4) to allow the second working electrode 3 to execute the regeneration of silver chloride.

Figure 41:
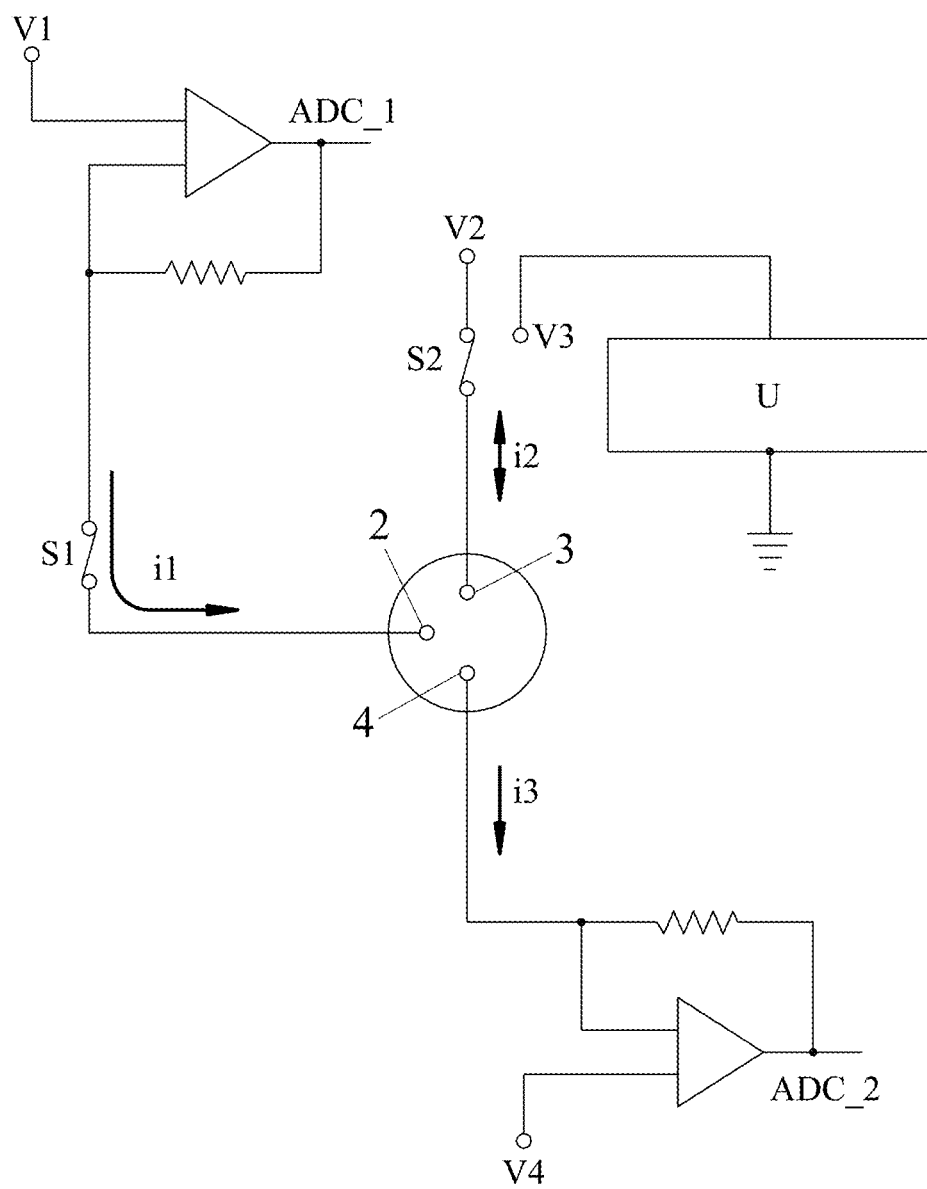
FIG. 41 is a circuit diagram illustrating another circuit design of Application Embodiment 4.

Alternatively, referring specifically to FIG. 41, the second working electrode 3 having the potential V2 is connected to a control unit (U) so as to adjust the amount of the thus regenerated silver chloride obtained by each of the regenerations of the silver chloride. For example, the consumption amount of silver chloride present in the counter electrode 4 corresponds to the physiological signal. When the third potential difference is constant, an execution time of step d) (i.e., a step of regeneration of the silver chloride) is dynamically modified according to the consumption amount of the silver halide. When the execution time of step d) is constant, the third potential difference is dynamically modified according to the consumption amount of the silver halide.

Figure 42:
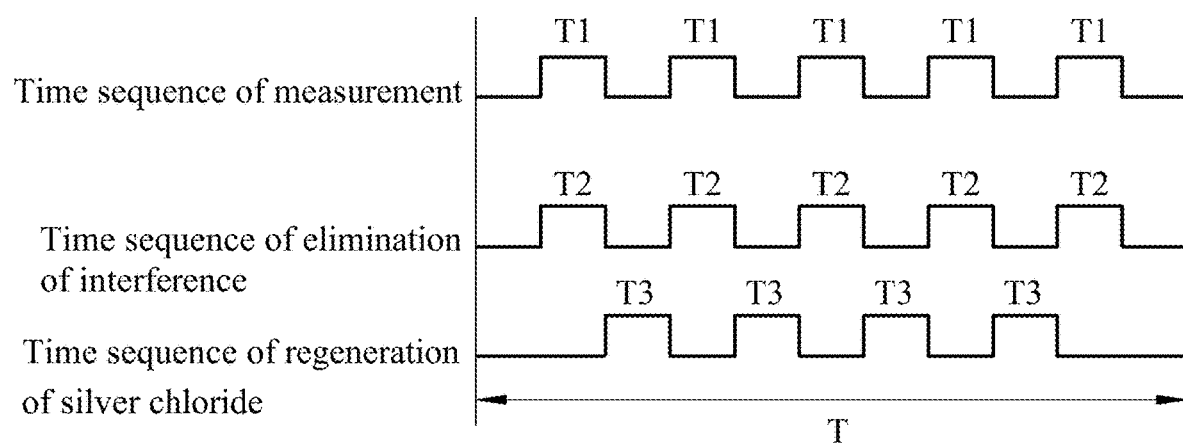
FIG. 42 is a schematic time-sequence diagram illustrating an operation time sequence of Application Embodiment 4.

Referring specifically to FIG. 42, the detecting time period (T) includes five of the first time sections (T1), five of the second time sections (T2), and four of the third time sections (T3). The first working electrode 2 executes the measurement of the analyte intermittently during the detecting time period (T). The measurement executed by the first working electrode 2 and the consumption of the interference executed by the second working electrode 3 are implemented simultaneously. In other words, the first time sections (T1) fully overlap with the second time sections (T2), so as to reduce the interference of the interfering substance to the measurement of the analyte. When the measurement executed by the first working electrode 2 and the consumption of the interference executed by the second working electrode 3 are paused, the second working electrode 3 cooperates with the counter electrode 4 to execute the regeneration of the silver chloride. In other words, the third time sections (T3) do not overlap with the first time sections (T1) and the second time sections (T2). The second working electrode 3 in Application Embodiment 4 has two functions. Specifically, the second working electrode 3 not only cooperates with the counter electrode 4 to execute the consumption of the interference during the second time sections (T2), but also cooperates with the counter electrode 4 to execute the regeneration of the silver chloride during the third time sections (T3).

Application Embodiment 5

The operation procedures for Application Embodiment 5 are substantially similar to those of Application Embodiment 4 except for the following differences.

In Application Embodiment 5, regeneration of the silver chloride is executed by applying the third potential difference between the counter electrode 4 and the first working electrode 2 to permit the potential V4 of the counter electrode 4 to be higher than the potential V1 of the first working electrode 2. Specifically, the first working electrode 2 in Application Embodiment 5 may not only cooperate with the counter electrode 4 to consume the interference during the second time sections (T2), but also cooperate with the counter electrode 4 to regenerate the silver halide during the second time sections (T3). That is, the first working electrode 2 has two functions herein.

Referring specifically to FIG. 36, in a variation of Application Embodiment 1, during the detecting time period (T), switch S1 is maintained in a close-circuit state, so as to permit the first working electrode 2 to cooperate with the counter electrode 4 to execute the measurement of the analyte, and switch S2 is switched cyclically and alternately between an open-circuit state and a close-circuit state, so as to permit the second working electrode 3 to cooperate intermittently with the counter electrode 4 to execute the consumption of the interference. In addition, in certain embodiments, the first time section (T1) may not overlap with the second time sections (T2), and second time sections (T2) may partially overlap with the third time sections (T3).

Application Example 1: In Vitro Elimination of the Interference

The in vitro elimination of the interference was carried out using the Embodiment 4 of the implantable micro-biosensor according to the operation procedures of Application Embodiment 1. The interference to be consumed was acetaminophen.

Figure 43:
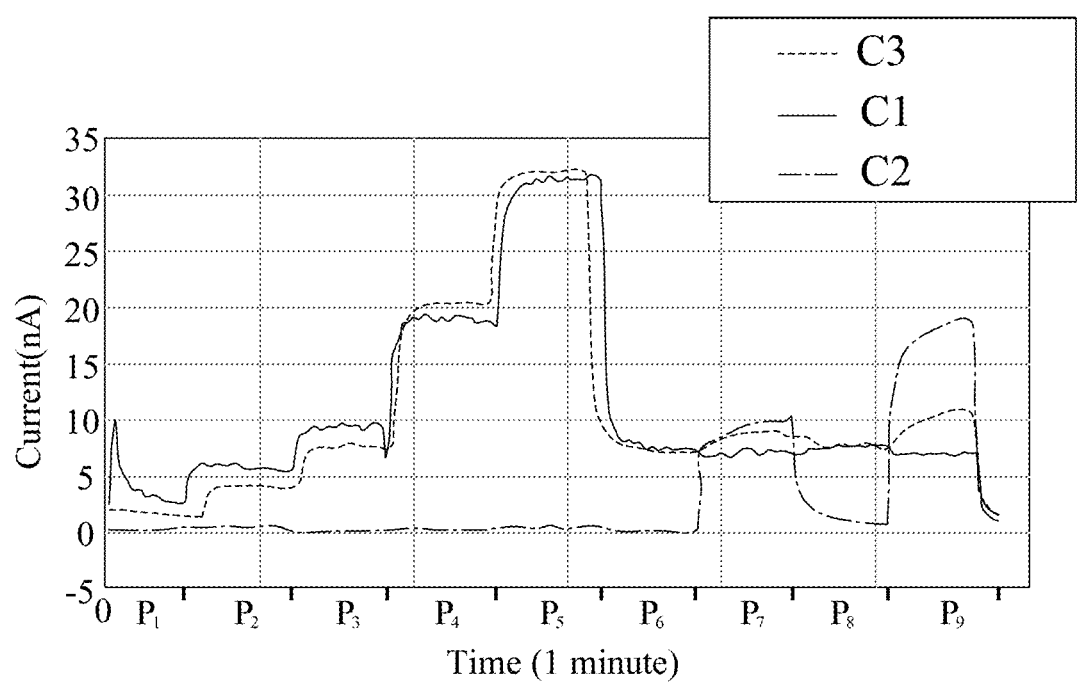
FIG. 43 is a graph plot of current signal versus time curves to illustrate the result of in vitro elimination of interference of Application Example 1, in which curve C1 shows current signals measured at the first sensing section when the second working electrode is switched on for the elimination of the interference, curve C2 shows current signals measured at the second sensing section when the second working electrode is switched on for the elimination of the interference, and curve C3 shows current signals measured at the first sensing section when the second working electrode is not switched on for the elimination of the interference.

Referring to FIG. 43, during difference time periods ($P_1$ to $P_9$), the implantable micro-biosensor was immersed sequentially in a phosphate buffered saline solution, a 40 mg/dL glucose solution, a 100 mg/dL glucose solution, a 300 mg/dL glucose solution, a 500 mg/dL glucose solution, a 100 mg/dL glucose solution, a 100 mg/dL glucose solution blended with 2.5 mg/dL acetaminophen, a 100 mg/dL glucose solution, and a 100 mg/dL glucose solution blended with 5 mg/dL acetaminophen. The results are shown in FIG. 43, in which curve 1 represents the current signal measured by the first sensing section 20 when the second working electrode 3 did not execute the interference consumption, curve 2 represents the current signal measured by the first sensing section 20 while the second working electrode 3 executes the consumption of the interference, and curve 3 represents the current signal measured by the second sensing section 30 while the second working electrode 3 executes the consumption n of the interference.

As shown by curve 3 in FIG. 43, the first sensing section 20 does not measure a current signal in the phosphate buffered saline solution. When the concentration of the glucose solution is increased, the current signal measured by the first sensing section 20 is increased accordingly. However, compared to the current signal measured by the first sensing section 20 during the time period P3, the current signal measured by the first sensing section 20 in the 100 mg/dL glucose solution blended with 2.5 mg/dL acetaminophen during the time period P7 is higher, indicating that the measured current signal during the time period P7 is interfered by acetaminophen. Furthermore, the current signal measured by the first sensing section 20 in the 100 mg/dL glucose solution blended with 5 mg/dL acetaminophen during the time period P9 is even higher, indicating that the measured current signal during the time period P9 is significantly interfered by acetaminophen.

Contrarily, as shown by curve C1 and curve C2 in FIG. 43, when the implantable micro-biosensor was immersed in the 100 mg/dL glucose solution blended with 2.5 mg/dL acetaminophen during the time period P7, the current signal measured by the first sensing section 20 is substantially the same as that measured during the time period P3, indicating that the current signal measured by the first sensing section 20 is not interfered by acetaminophen when the second working electrode 3 is switched to execute the consumption of the interference. In addition, the second sensing section 30 of the second working electrode 3 is used for oxidizing acetaminophen so as to consume acetaminophen. Therefore, no current signal is detected by the second sensing section 30 in the phosphate buffered saline solution and the glucose solutions without acetaminophen, and a current signal measured by the second sensing section 30 is present in the glucose solutions containing acetaminophen. It is indicated that when a measurement environment (i.e. the measuring region) contains acetaminophen, the acetaminophen can be consumed by the second sensing section 30, such that the glucose measurement executed by the first sensing section 20 is not interfered by acetaminophen. Therefore, the implantable micro-biosensor of the disclosure can be used for accurately monitoring a physiological parameter of an analyte.

Application Example 2: In Vivo Elimination of the Interference

The in vivo elimination of the interference was carried out using Embodiment 4 of the implantable micro-biosensor according to the operation procedures of Application Embodiment 1. The interference to be consumed was acetaminophen (i.e., medical interference). The implantable micro-biosensor cooperates with a base and a transmitter to constitute a continuous glucose monitoring system. The implantable micro-biosensor is hold on to the skin of a subject by the carrier and is partially implanted under the skin to measure a physiological signal in response to a glucose concentration. The transmitter is combined with the base and is connected to the implantable micro-biosensor so as to receive and process the physiological signal measured by the implantable micro-biosensor. The subject took two tablets of Panadol® (acetaminophen, 500 mg), and a time period of medical interference ranges from 4 to 6 hours after taking the tablets. The results are shown in FIGS. 44 to 47.

Figure 44:
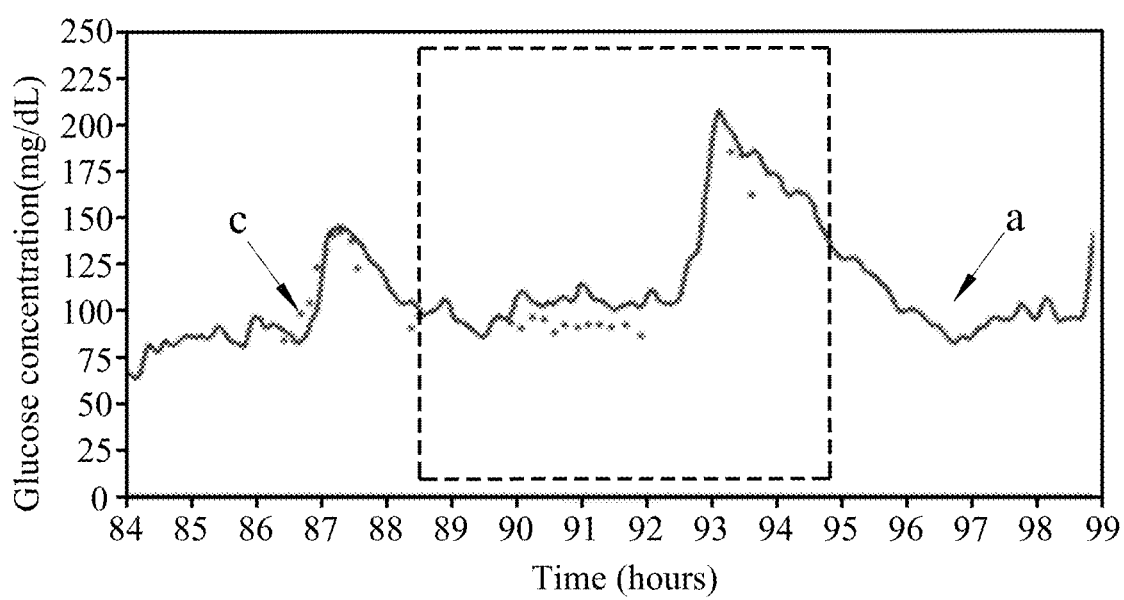
FIG. 44 is graph plot of glucose concentration versus time curve to illustrate the measurement result of glucose concentration in a body over the measurement time period without execution of the elimination of the interference, in which a portion indicated by a dashed-line frame represents a time period of medical interference, curve (a) represents a measurement result of the first working electrode, and a plurality of dots (c) represent glucose concentration values measured with a conventional test strip using an analyzing instrument.
Figure 45:
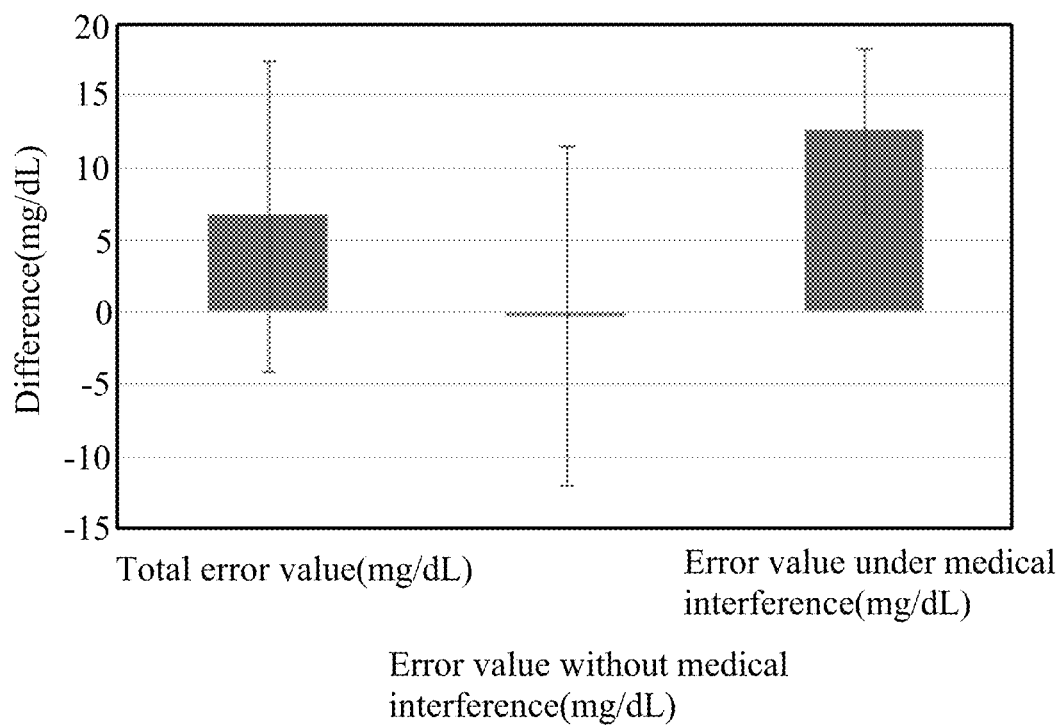
FIG. 45 is a bar chart illustrating the difference of the measurement result of FIG. 44 under the medical interference and without the medical interference.
Figure 46:
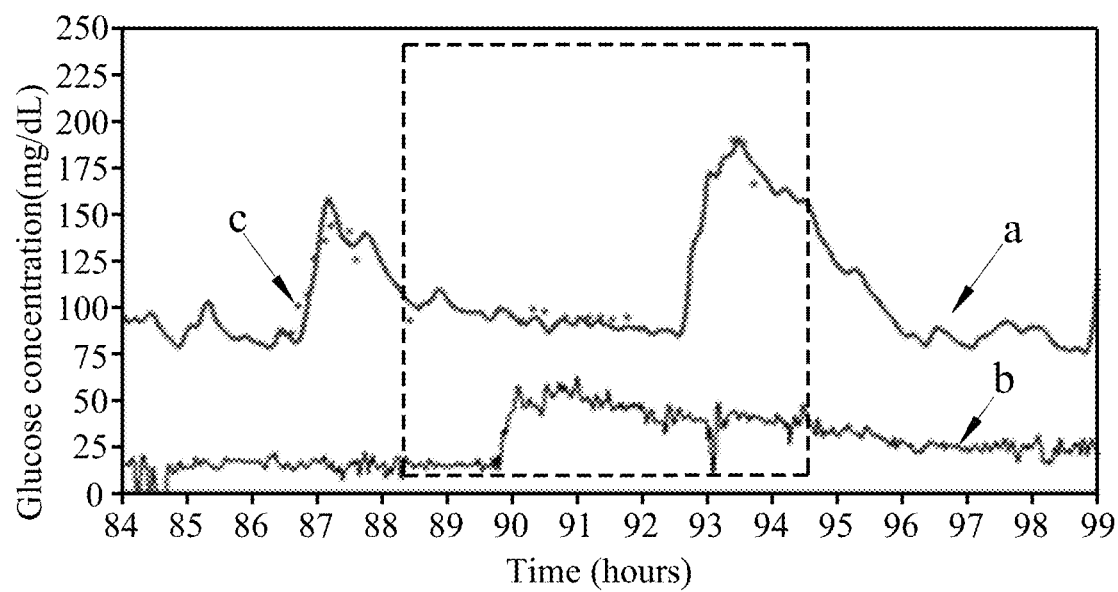
FIG. 46 is graph plot of glucose concentration versus time curves to illustrate the measurement result of glucose concentration in a body over the measurement time period with execution of the elimination of the interference, in which a portion indicated by a dashed-line frame represents the time period of the medical interference, curve (a) represents a measurement result of the first working electrode, curve (b) represents a measurement result of the second working electrode, and a plurality of dots (c) represent glucose concentration values measured with a conventional test strip using an analyzing instrument.
Figure 47:
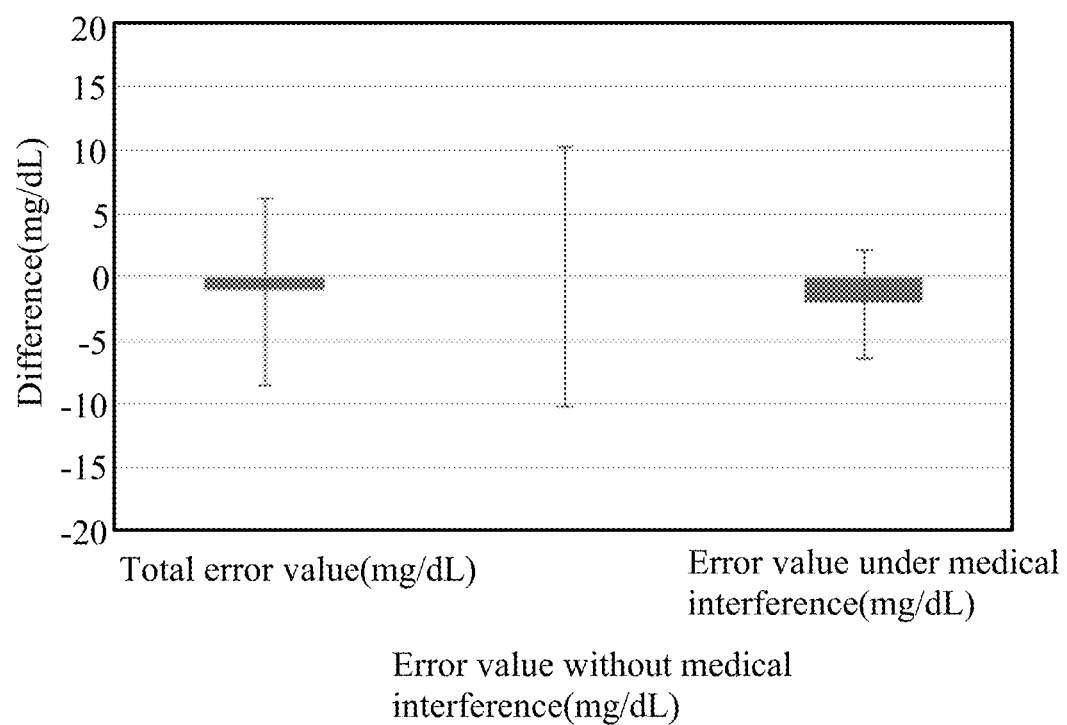
FIG. 47 is a bar chart illustrating the difference of the measurement result of FIG. 46 under the medical interference and without the medical interference.

FIG. 44 is graph plot of a glucose concentration versus time curve to illustrate the measurement result of the glucose concentration in a subject over the measurement time period without consumption of the interference, in which a portion indicate by a dashed-line frame represents a time period of medical interference, curve (a) represents a measurement result of the first working electrode 2, and a plurality of dots (c) represent glucose concentration values measured with a conventional test strip using an analyzing instrument. FIG. 45 is a bar chart illustrating the difference of the measurement result of FIG. 44 under the medical interference and without the medicine interference. FIG. 46 is graph plot of a glucose concentration versus time curves to illustrate the measurement result of the glucose concentration in the subject over the measurement time period with consumption of the interference, in which a portion indicated by a dashed-line frame represents the time period of medical interference, curve (a) represents a measurement result of the first working electrode 2, curve (b) represents a measurement result of the second working electrode 3, and a plurality of dots (c) represent glucose concentration values measured with a conventional test strip using an analyzing instrument. FIG. 47 is a bar chart illustrating the difference of the measurement result of FIG. 46 under the medical interference and without the medical interference.

As shown in FIGS. 44 and 45, when the implantable micro-biosensor is not subjected to consumption of the interference, the values measured during a time period under the medical interference is higher than the values measured using the conventional test strip. An average error value during the time period without the medical interference is −0.2 mg/dL. An average error value during the time period of the medical interference is 12.6 mg/dL. A total error value is 6.7 mg/dL. A mean absolute relative difference during the time period of the medical interference is 10.6.

As shown in FIGS. 46 and 47, when the implantable micro-biosensor is subjected to consumption of the interference, the measurement results under the medical interference is substantially the same as those obtained using the conventional test strip, and the average error value during the time period without the medical interference is 0.1 mg/dL. The average error value during the time period of the medical interference is −2.1 mg/dL. The total error value is −1.1 mg/dL. The mean absolute relative difference during the time period of the medical interference is 4.6.

The aforesaid results demonstrated that when the implantable micro-biosensor of the disclosure is subjected to consumption of the interference, the error value can be reduced significantly, such that the measurement accuracy can be enhanced.

In summary, in the implantable micro-biosensor according to the disclosure, the first working electrode, the at least one second working electrode, and the at least one counter electrode are included, and a relative position of the first sensing section and the second sensing section is assigned, such that the implantable micro-biosensor according to the disclosure not only can execute the measurement of the analyte and reduce the influence of the interfering substances, but also can regenerate the silver halide by applying a potential difference to the counter electrode. Measurement of the analyte, reduction of the influence of the interfering substances, and regeneration of the silver halide can be adjustably performed according to practical needs. Therefore, the implantable micro-biosensor according to the disclosure can perform an accurate measurement of an analyte and has an extended service life, and can monitor a physiological parameter of an analyte continuously.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for manufacturing an implantable micro-biosensor, comprising the steps of:
   a) providing a substrate having a first surface, wherein the first surface has a first sensing region to be implanted subcutaneously for measuring a physiological parameter of an analyte in a biological fluid;
   b) forming on the first surface of the substrate a first working electrode which at least includes a first sensing section, a surface material of the first sensing section including a first conductive material;
   c) forming on the first surface of the substrate at least one second working electrode which at least includes a second sensing section disposed proximate to at least one side of the first sensing section, a surface material of the second sensing section including a second conductive material different from the first conductive material, wherein both the second sensing section and the first sensing section are located at the first sensing region; and
   d) forming a chemical reagent layer which at least covers the first conductive material of the first sensing section and which reacts with the analyte to produce a product, wherein steps b) and c) are implemented simultaneously by the sub-steps of:
      b1) applying the second conductive material on the first surface of the substrate;
      b2) subjecting the second conductive material to patterning so as to divide the second conductive material into a first area and at least one second area separated from each other; and
      b3) applying the first conductive material at the first sensing region to cover at least a portion of the second conductive material of the first area to form the first sensing section of the first working electrode and to configure the second conductive material at the at least one second area as the at least one second working electrode.

2. The method according to claim 1, wherein step b) further includes, after sub-step b2), a sub-step of forming a first insulation layer on the first surface of the substrate so as to define the first sensing region on the first surface of the substrate.

3. The method according to claim 1, wherein the second sensing section is formed to be spaced apart from the at least one side of the first sensing section by a distance of up to 0.2 mm.

4. The method according to claim 1, wherein the second sensing section is formed to extend along and be spaced apart from at least a portion of a periphery of the first sensing section, such that a ratio of the portion of the periphery of the first sensing section to a total of the periphery of the first sensing section ranges from 30% to 100%.

5. The method according to claim 1, wherein sub-step b2) forms two of the at least one second area so as to permit the second sensing section of each of two of the at least one second working electrode to be formed in sub-step b3), wherein second sensing sections of two of the the at least one second working electrode are disposed, respectively, along two opposite sides of the first sensing section of the first working electrode.

6. The method according to claim 1, wherein sub-step b1) is implemented by a screen printing process.

7. The method according to claim 1, wherein sub-step b3) is implemented by a plating process.

8. The method according to claim 1, wherein sub-step b2) is implemented by a laser engraving process.

9. The method according to claim 1, wherein step d) is implemented by immersing the substrate formed with the first and second working electrodes into a solution containing a chemical reagent.

10. The method according to claim 9, wherein the chemical reagent simultaneously covers the first conductive material of the first sensing section and the second conductive material of the second sensing section.

11. The method according to claim 1, wherein the first conductive material is selected from the group consisting of a noble metal, a noble metal derivative, and a combination thereof, and the noble metal is selected from the group consisting of gold, platinum, palladium, iridium, and combinations thereof.

12. The method according to claim 1, comprising an additional step:
   e) forming on the substrate a counter electrode which cooperates with the first working electrode to measure the physiological parameter of the analyte.

13. The method according to claim 12, comprising another additional step:
   f) forming on the substrate a reference electrode which is spaced apart from the counter electrode and which is free of an electrical connection with the counter electrode.

14. The method according to claim 13, wherein steps e) and f) are implemented simultaneously by sub-steps including:
- i) forming a backing material layer on a second surface of the substrate which is opposite to the first surface of the first surface;
- ii) subjecting the backing material layer to patterning so as to divide the backing material layer into a third area and a fourth area which are separated from each other and which are free of an electrical connection with each other, such that the backing material layer at the third area is configured as the counter electrode; and
- iii) forming a reference electrode material on at least a portion of the backing material layer at the fourth area to obtain the reference electrode.

15. The method according to claim 14, further comprising a sub-step after sub-step ii), of forming a second insulation layer on the second surface of the substrate so as to define a second sensing region.

16. The method according to claim 13, wherein steps of e) and f) are implemented simultaneously by sub-steps including:
- i') forming a backing material layer on a second surface of the substrate which is opposite to the first surface of the substrate;
- ii') applying a precursor material on at least a portion of the backing material layer;
- iii') subjecting the backing material layer and the precursor material to patterning so as to divide the second surface into a third area and a fourth area which are separated from each other and which are free of an electrical connection with each other, such that the backing material layer at the third area is configured as the counter electrode and at least a portion of the backing material layer at the fourth area is covered with the precursor material; and
- iv') converting the precursor material on the backing material layer at the fourth area to a reference electrode material to obtain the reference electrode.

17. The method according to claim 16, wherein the backing material layer is formed as a layered-configuration selected from the group consisting of a single-layered configuration and a multi-layered configuration, each of which is made from a material selected from the group consisting of carbon, silver, a combination thereof.

18. The method according to claim 16, further comprising a sub-step after sub-step iii'), of forming a second insulation layer on the second surface of the substrate so as to define a second sensing region.

* * * * *